United States Patent
Franco

(10) Patent No.: US 7,291,597 B2
(45) Date of Patent: *Nov. 6, 2007

(54) GROWTH FACTOR THERAPY MOBILIZATION OF STEM CELLS INTO THE PERIPHERAL BLOOD

(76) Inventor: Wayne P. Franco, 500 Cold Spring Rd., No. E217, Rocky Hill, CT (US) 06067

( * ) Notice: Subject to any disclaimer, the term of this patent is extended or adjusted under 35 U.S.C. 154(b) by 0 days.

This patent is subject to a terminal disclaimer.

(21) Appl. No.: 11/029,449

(22) Filed: Jan. 5, 2005

(65) Prior Publication Data

US 2005/0158858 A1 Jul. 21, 2005

Related U.S. Application Data

(60) Continuation-in-part of application No. 10/731,197, filed on Dec. 9, 2003, which is a division of application No. 09/828,330, filed on Apr. 6, 2001, now Pat. No. 6,759,386.

(60) Provisional application No. 60/195,624, filed on Apr. 6, 2000.

(51) Int. Cl.
*A61K 38/00* (2006.01)
*A61K 48/00* (2006.01)

(52) U.S. Cl. .................. 514/12; 424/93.21

(58) Field of Classification Search .......... None
See application file for complete search history.

(56) References Cited

U.S. PATENT DOCUMENTS

| | | | |
|---|---|---|---|
| 5,932,540 A | 8/1999 | Hu et al. ................ 514/2 |
| 6,352,971 B1 | 3/2002 | Deisher et al. .......... 514/2 |
| 6,482,406 B1 | 11/2002 | Stewart ............. 424/93.21 |
| 6,608,182 B1 | 8/2003 | Rosen et al. ........... 530/399 |
| 6,673,604 B1 | 1/2004 | Edge .................. 435/347 |
| 6,716,626 B1 | 4/2004 | Itoh et al. ............ 435/325 |
| 6,734,285 B2 | 5/2004 | Hu et al. ............. 530/350 |
| 6,775,574 B1 | 8/2004 | Soykan et al. .......... 607/50 |
| 6,852,533 B1* | 2/2005 | Rafii et al. .......... 435/372 |
| 7,166,280 B2* | 1/2007 | Franco ............... 424/93.7 |
| 2002/0090722 A1 | 7/2002 | Dominko et al. ........ 435/366 |
| 2002/0142457 A1 | 10/2002 | Umezawa ............ 435/366 |
| 2002/0172663 A1 | 11/2002 | Palasis .............. 424/93.2 |
| 2003/0022367 A1 | 1/2003 | Xu .................. 435/366 |
| 2003/0023995 A1* | 1/2003 | Benezra .............. 800/10 |
| 2003/0082148 A1* | 5/2003 | Ludwig et al. ........ 424/93.7 |
| 2003/0103951 A1 | 6/2003 | Pittenger et al. ...... 424/93.21 |
| 2003/0199464 A1 | 10/2003 | Itescu ............... 514/44 |
| 2003/0211994 A1 | 11/2003 | Li et al. ............. 514/12 |
| 2003/0219898 A1 | 11/2003 | Sugaya et al. ......... 435/455 |
| 2004/0018174 A1* | 1/2004 | Palasis .............. 424/93.7 |
| 2004/0028658 A1 | 2/2004 | Faustman ............ 424/93.7 |
| 2004/0033214 A1 | 2/2004 | Young et al. ......... 424/93.7 |
| 2004/0048375 A1 | 3/2004 | Alt .................. 435/373 |
| 2004/0071665 A1 | 4/2004 | Xiao et al. ........... 424/93.7 |
| 2004/0071687 A1 | 4/2004 | Rafii et al. .......... 424/94.63 |
| 2004/0096936 A1 | 5/2004 | Deisher et al. ........ 435/69.1 |
| 2004/0107453 A1 | 6/2004 | Furcht et al. .......... 800/18 |
| 2004/0131585 A1 | 7/2004 | Itescu ............... 424/85.1 |
| 2004/0131601 A1 | 7/2004 | Epstein et al. ........ 424/93.21 |
| 2004/0161412 A1 | 8/2004 | Penn et al. ........... 424/93.7 |
| 2004/0161421 A1 | 8/2004 | Komowski et al. ...... 424/93.21 |
| 2005/0026220 A1* | 2/2005 | Rafii et al. ........... 435/7.2 |
| 2005/0069527 A1* | 3/2005 | Laughlin et al. ........ 424/93.7 |

OTHER PUBLICATIONS

Mathur, A; Martin, JF, "Stem Cells And Repair Of The Heart", *Lancet* Jul. 10, 2004;364 (9429): 183-192.

Fijnvandraat, AC; Morman, AF, "Stem Cells: biology and possible application to myocardial infarct", *Ned Tijdschr. Geneeskd* Jun. 12, 2004: 148 (24): 1186-91.

Aschermann, M; Horak, J; Linhard A; Aschermann, O, "Use Of Stem Cells For Myocardial Regeneration", *Cas Lek Cesk.* 2004; 143 (2): 71-4.

Murry, CE; Soonpaa MH et al., "Haematopoietic Stem Cells Do Not Transdifferentiate Into Cardiac Myocytes In Myocardial Infarcts", *Nature* Apr. 8, 2004; 428 (6983); 664-8. Epub Mar. 21, 2004.

Fraser JK; Schreiber RE et al., "Adult Stem Cell Therapy For The Heart", *International Journal of Biochemistry And Cell Biology* Apr. 2004; 36 (4): 658-66.

Strauer, BE; Brehm M et al., "Stem Cell Therapy In Acute Myocardial Infarction", *Med Klin* (Munich). Dec. 15, 2003: 98 Supplement 2: 14-8.

Masino, AM; Gallardo, TD; Wilcox, CA, et al., "Transcriptional Regulation of Cardian Progenitor Cell Populations", *Circulation Research* 95: 389-397, Aug. 2004.

Melo, LG; Pachori, AS, et al., "Gene and Cell-Based Therapies For Heart Disease", *FASEB J.* Apr. 2004; 18 (6): 648-63.

* cited by examiner

*Primary Examiner*—David S Romeo
*Assistant Examiner*—Daniel C Gamett
(74) *Attorney, Agent, or Firm*—Ernest D. Buff & Associates, LLC; Ernest D. Buff; Theodore J. Pierson

(57) ABSTRACT

Stem cells are mobilized into the peripheral blood by a method comprising the steps of: (i) administering to an individual at least one of the following: FGF1 and FGF2, and also at least one of the following: VEGF, VEGFA and VEGF165; (ii) isolating the peripheral blood stem cells (PBSC) by apheresis; and (iii) injecting the PBSC into a patient suffering from chronic heart disease. Alternatively, gene therapy is used for the induction of the stem cells into the peripheral blood, wherein the gene therapy formulation comprises AD5FGF-4 or VEGF165 plasmid DNA. Additionally, the progress of the treatment of the chronic heart disease is monitored by using an echocardiogram unit.

30 Claims, 4 Drawing Sheets

FIG. 1

GROWTH FACTOR THERAPY MOBILIZATION OF STEM CELLS INTO THE PERIPHERAL BLOOD

REFERENCE TO RELATED APPLICATIONS

This is a continuation-in-part of application Ser. No. 10/731,197, filed Dec. 9, 2003 which, in turn, is a division of application Ser. No. 09/828,330, filed Apr. 6, 2001, now U.S. Pat. No. 6,759,386 which, in turn, claimed the benefit of Application No. 60/195,624, Filed Apr. 6, 2000.

BACKGROUND OF THE INVENTION

1. Field of the Invention

The present invention relates generally to the isolation of peripheral blood stem cells, and more particularly to the mobilization of stem cells into the peripheral blood by growth factors and/or gene therapy, to be used for the treatment of heart disease.

2. Description of the Prior Art

Chronic myocardial ischemia is the leading cardiac illness affecting the general population in the Western world. Since the occurrence of angina symptoms or objective physiological manifestations of myocardial ischemia signifies a mismatch between myocardial oxygen demand and the available coronary blood flow, the goal of therapy is to restore this balance. This can be achieved either by attempting to prevent further disease progression through modification of risk factors, or by more aggressive modes of therapy such as reducing the myocardial oxygen demand (i.e. reducing the heart rate, myocardial contractility or blood pressure) by using anti-anginal medications, or by restoring the blood supply by means of mechanical interventions such as percutaneous transluminal angioplasty or its variants, or coronary artery bypass surgery, coronary angioplasty (PTCA) or bypass surgery (CABG).

Many tissues in the body fail to regenerate independently after injury or other environmental stresses, and intervention may be required to restore function to those tissues. The intrinsic repair mechanisms of the heart are often inadequate to restore function after a myocardial infarction. Thus, destroyed cardiomyocytes are not effectively replaced. The remaining cardiomyocytes are unable to reconstitute tissue lost to necrosis, and heart function deteriorates over time.

Recent attempts to ameliorate the damage caused by myocardial infarction or other disease processes have been directed to regenerating myocardial tissue by implanting a variety of stem and progenitor cells that can differentiate into cardiac muscle. Adult-derived bone marrow cells have been shown to regenerate cardiomyocytes following an infarction.

Stem cells have the capacity, upon division, for both self-renewal and differentiation into progenitors. Thus, dividing stem cells generate both additional primitive stem cells and somewhat more differentiated progenitor cells. In addition to the well-known role of stem cells in the development of blood cells, stem cells also give rise to cells found in other tissues, including but not limited to the liver, brain, pancreas, kidney, muscle, upper and lower gastrointestinal tracts, and heart.

Stem cells have the ability to divide indefinitely, and to specialize into specific types of cells. Due to the regenerative properties of stem cells, they have been considered an untapped resource for potential engineering of tissues and organs. It would be a major advancement in science to provide uses of stem cells with respect to addressing cardiac conditions.

Although, after birth, stem cells and progenitor cells are located almost exclusively in the bone marrow, they nevertheless exhibit migratory properties; that is to say, under physiological conditions, they migrate through the cavities of the bone marrow and pass into circulation. That process, commonly known as "mobilization", can be amplified by various treatments.

Studies have demonstrated that peripheral blood stem cells (PBSC) infused in a host exhibit enhanced potential for engraftment as compared to bone marrow-derived stem and progenitor cells. Mobilized PBSC are currently used in both autologous and non-autologous transplantation settings.

Several growth factors, such as G-CSF, GM-CSF, and ERYPHROPOIETIN have been indicated as mobilizing agents and are currently used to increase the number of PBSC prior to apheresis. Treatments able to increase the number of stem cells in the peripheral blood are of great interest in order to mobilize a large set of stem cells, thus reducing the number of apheresis procedures required to collect a sufficient amount of stem cells to be transplanted. The possibility of obtaining an increased amount of stem cells in the peripheral blood has for years been the subject of intensive research activity.

SUMMARY OF THE INVENTION

The present invention provides a superior method for obtaining peripheral blood stem cells (PBSC) using a growth factor formulation comprising specific variants of FGF and VEGF.

In one aspect the invention provides a method for obtaining PBSC by first administering a growth factor formulation to an individual comprising at least one of the following: FGF1 and FGF2, and also at least one of the following: VEGF, VEGFA and VEGF165. Alternatively, or in combination with the growth factor formulation, gene therapy is used to obtain PBSC, wherein the gene therapy formulation comprises AD5FGF-4 or VEGF165 plasmid DNA. The PBSC are then isolated from the individual's peripheral blood by apheresis. The PBSC are then injected into a patient suffering from chronic heart disease. The patient may be the same individual whose PBSC are being isolated or the patient may be an HLA matched patient.

The growth factor formulation may be administered in a single dose or administered in repeated doses. The growth factor formulation may be administered intravenously, orally, subcutaneously, intranasally, intramuscularly, intracoronary, or by inhalation therapy. The growth factor formulation may also be directly injected into the heart.

A second aspect of the invention provides a method for obtaining PBSC by first administering to an individual a growth factor formulation comprises at least one of the following: FGF1 and FGF2, and also at least one of the following: VEGF, VEGFA and VEGF165. Alternatively, gene therapy is used for the induction of the stem cells into the peripheral blood, wherein the gene therapy formulation comprises AD5FGF-4 or VEGF165 plasmid DNA. The PBSC are isolated from the individual's peripheral blood by apheresis. The PBSC are then frozen and stored. At a later time the PBSC are thawed and injected into a patient suffering from chronic heart disease. The patient may be the same individual whose PBSC are being isolated or the patient may be an HLA matched patient.

The specific combination of the above-identified growth factors and/or gene therapy provides a superior method for mobilizing stem cells into the peripheral blood. This specific combination of growth factors works synergistically to mobilize PBSC. This method allows a greater yield of stem cells from a single apheresis procedure and thus decreases the number of apheresis procedures necessary to collect sufficient PBSC.

BRIEF DESCRIPTION OF THE DRAWINGS

The invention will be more fully understood and further advantages will become apparent when reference is had to the following detailed description of the preferred embodiments of the invention and the accompanying drawings, wherein like reference numerals denote similar elements throughout the several views, and in which:

FIG. 1 is an illustration of the lung, indicating a mechanism of delivery of aerosol drug articles through the lung and into the bloodstream;

DETAILED DESCRIPTION OF THE INVENTION

Figure 2:
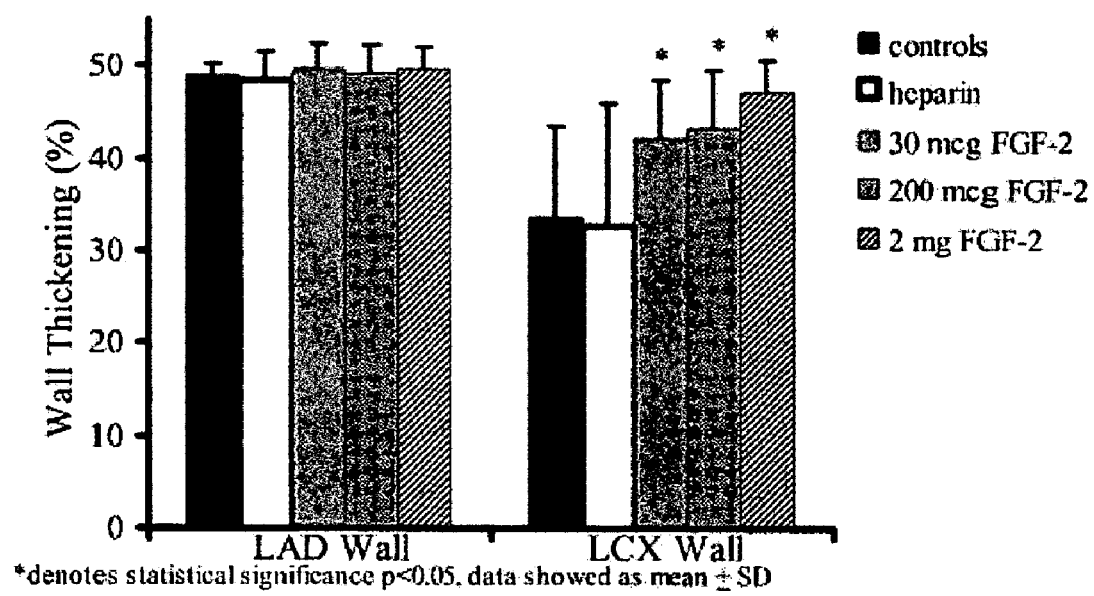
FIG. 2 is an illustration of the results of measured regional wall thickening in the LAD (normal) and LCX (collateral-dependent) distribution.

Generally stated, the invention relates to the mobilization of stem cells into the peripheral blood by administering to an individual a growth factor formulation comprising at least one of the following: FGF1 and FGF2, and also at least one of the following: VEGF, VEGFA and VEGF165. Alternatively, gene therapy is used for the induction of the stem cells into the peripheral blood, wherein the gene therapy formulation comprises AD5FGF-4 or VEGF165 plasmid DNA. The stem cells will be isolated from the peripheral blood and either stored or injected into a patient. The population of isolated stem cells is administered into a patient suffering from heart disease whereby the injection of the stem cells ameliorates the heart disease. Additionally, the progress of the treatment of the heart disease is monitored by using an echocardiogram unit.

It has now surprisingly been found that it is possible to obtain increased mobilization of stem cells by the administration of a growth factor formulation that comprises at least one of the following: FGF1 and FGF2, and also at least one of the following: VEGF, VEGFA and VEGF165. This combination of at least two growth factors acts synergistically to mobilize stem cells into the peripheral blood.

To obtain an optimal yield of peripheral blood stem cells (PBSC), the growth factors and/or gene therapy are administered to the patient or donor prior to harvesting the peripheral blood to mobilize the PMSC. By "mobilization" is meant an increase in the population of stem cells or specific subpopulations of cells in peripheral blood. As used herein, "mobilization factors" are proteins or other chemical agents that, when administered to a donor, increase the number of stem cells present in the peripheral blood of the donor.

The growth factors can be administered in any effective manner, including orally, intranasally, intravenously, subcutaneously, intramuscularly, intracoronary, intramyocardially, or by inhalation therapy. Preferably, the growth factors are initially administered intravenously. The growth factors can be administered in a single dose prior to harvesting the PBSC or in repeated doses administered over several days prior to harvesting. Preferably, the growth factors are first given intravenously followed by repeated doses by inhalation therapy or intravenously. Alternatively, or in combination with the growth factor delivery, gene therapy is used to induce the stem cells into the peripheral blood.

Both the growth factor approach and gene therapy approach for the induction of the stem cells also operate to prime the heart and to traffic the stem cells into the heart. The stem cells require blood flow and protection from ischemia. Therefore, this approach traffics the stem cells to the damaged area of the heart, improves blood flow and provides protection against ischemic damage.

Intrapulmonary inhalation therapy, preferably via dry powder formulations, offers significant advantages over previous delivery strategies. Formulation and delivery technology has reached a state where a number of therapeutic macromolecules, including insulin, can now be delivered consistently, and at clinically effective levels via inhalation therapy. An added advantage arising from the non-invasive nature of inhalation therapy is that it is particularly attractive in treatments requiring repeated dosing over longer time intervals.

Pulmonary Routes of Administration Pulmonary delivery of potentially therapeutic agents provides a direct route to the circulation, with a minimum amount of discomfort and pain, and is a cost-effective alternative in comparison to the more invasive routes of delivery typically utilized for administration of FGF, VEGF, and related proteins. Traditionally, noninvasive delivery systems do not work for macromolecules; for example, pills or tablets enter the stomach, where enzymes and hydrochloric acid rapidly degrade the protein or peptide. The oral administration of proteins and peptides is under investigation, but no satisfactory system is commercially available yet. No acceptable transdermal delivery systems have been found because of the proteins' size constraints or inherent physical properties that prohibit these large molecules from crossing the diverse layers of the skin without the addition of irritating enhancers.

Figure 1:
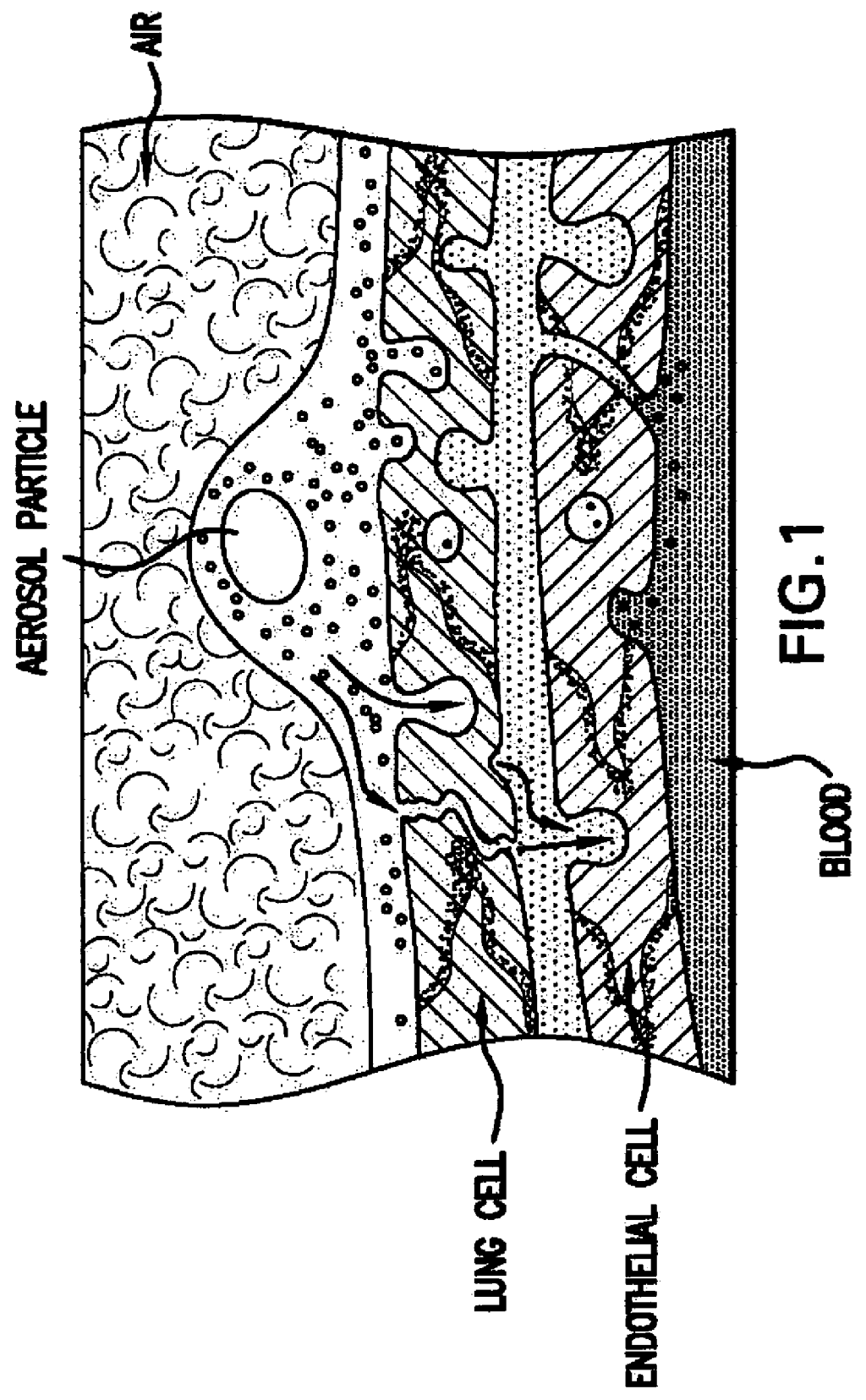

The biology of the lung makes it a favorable environment for noninvasive drug delivery (see FIG. 1). Studies have shown that most large-molecule agents are absorbed naturally by the lungs, and once absorbed in the deep lung, they pass readily into the bloodstream without the need for enhancers, which are normally used by other noninvasive routes. Patton, J. S. *Adv. Drug Delivery Rev.* 1996, 19, 3. During inhalation, air passes through the trachea, which branches more than 17 times into successively smaller tubes that constitute the bronchial network, eventually reaching the grapelike clusters of tiny air sacs known as alveoli. Each breath of air is distributed deep into the lung tissue, to the alveolar epithelium, the surface area of which measures ~~100 m2 in adults—roughly equivalent to the surface area of a standard singles tennis court. This large area is made up of about half a billion alveoli, from which oxygen passes into the bloodstream via an extensive capillary network.

The potentially most significant barrier to the delivery of compounds via the lungs is the tightly packed, single-cell-thick layer known as the pulmonary epithelium. In the lungs, the epithelium of the airway is very different from that of the alveolus. Thick, ciliated, mucus-covered cells line the surface of the airway, but the epithelial cell layer thins out as it reaches deeper into the lungs, until reaching the tightly packed alveolar epithelium. Most researchers believe that protein absorption occurs in the alveoli, where the body absorbs peptides and proteins into the bloodstream by a natural process known as transcytosis.

Logically, there is little reason to expect safety problems related to the inhalation of a substance to be any different as compared with the injection of the same amount of that substance. A growing quantity of safety data indicates that inhaling proteins is safe for patients with both healthy and diseased lungs. The safety of therapeutic inhalation is further supported by the existence of more than 20 small-molecule and one large-protein drug inhalation products-approved by the U.S. Food and Drug Administration (FDA); this group of therapeutic inhalants contains 13 different excipients.

Most aerosol systems today deliver a total amount of <100 µg of drug per puff to the deep lung; this amount is too low to enable timely delivery of many macromolecules if the required dose is on the order of milligram doses. Traditional inhalation systems have been designed primarily to deliver some of the most potent drugs in use today, such as the bronchodilators and bronchosteroids to treat asthma. Both types of compounds are bioactive in the lung at 5-20 µg per dose. In contrast, many peptide and protein compounds need to be delivered to the deep lung at much larger doses of 2-20 mg. Adjei, A. L.; Gupta, P. K. *Inhalation Delivery of Therapeutic Peptides and Proteins*; Marcel Dekker: New York, 1997.

Bioavailability After the aerosolized drug reaches the deep lung, it must be absorbed with high enough bioavailability to make the system practical. As early as 1925, insulin inhalation for the treatment of diabetes was shown to work in humans, but the bioavailability was low (<3%). More recently, several inhalation studies comparing insulin administration by aerosol inhalation (using cumbersome devices) and by subcutaneous injection for the reproducibility of dosing have shown that the variability in glucose response to the two methods was equivalent. Bioavailability in more recent studies with aerosol insulin was up to 25%, supporting the use of such a method of administration. Laube, B. L.; Georgopolos, A.; Adams, G. K. *J. Am. Med. Assoc.* 1993, 269, 2106. Insulin administered by oral inhalation effectively normalized diabetic patients' plasma glucose levels without adverse effects. Numerous patents have issued, directed to methods, formulations and devices for the oral administration of insulin via inhalation therapy. See, for example, U.S. Pat. Nos. 5,952,008; 5,858,968; and 5,915,378, the disclosures of which are hereby incorporated specifically by reference.

Bioavailability studies in humans of the aerosol administration of lutenizing hormone-releasing hormone (LHRH), a decapeptide, and its analogues also have demonstrated that appropriate bioactive systemic levels can be achieved to treat conditions such as endometriosis and prostate cancer. Thus, using delivery and formulation technology available today, as is recognized by one of skill in the appropriate art, it is possible to deliver an effective amount of FGF and/or VEGF, and related growth factor proteins, and gene therapy, in the treatment of chronic and acute heart disease.

The mechanism of macromolecule absorption in the deep lung is thought to occur via normal physiological processes that can deliver active compounds with relatively high bioavailability without requiring the addition of penetration enhancers. LHRH analogues (used in treating osteoporosis), composed of 10 amino acids, can reach 95% bioavailability; however, interferon-$\alpha$, composed of 165 amino acids, attains 29% bioavailability. Some smaller peptides such as glucagon (29 amino acids) and somatostatin (28 amino acids) reach 1% bioavailability. The degree of bioavailability is thought to depend on the peptide or protein susceptibility to certain hydrolytic enzymes in the lung.

How a macromolecular drug is formulated also affects its delivery to the deep lung. Many macromolecules are formulated as dry powders because they are more stable as solids than as liquids. Compared with liquid aerosol particles, which are mostly water (97%), dry powder aerosol particles can carry 50-100% of the drug. In general, more puffs would be necessary to deliver the equivalent amount of drug to the alveolar epithelium from a liquid aerosol device as compared to a dry powder aerosol device. Liquid formulations also carry the risk of microbial growth; the risk of lung infections due to bacterial and fungal contaminants is greatly reduced with dry powder systems. By greatly lowering the possibility of microbial contamination, dry powder systems offer a safer technology.

In the liquid state, individual protein or peptide molecules are extremely mobile. When water is removed, macromolecules usually pack together in an amorphous state, unlike the highly ordered packing that occurs in crystallization. When water is removed from proteins, the protein molecules remain mobile and chemical stability stays low in the initial amorphous powder that forms. When a critical amount of water has been removed, a kind of molecular gridlock occurs, producing a greatly increased chemical stability called the "amorphous glass state." In this state, previously mobile molecules slow down drastically. As long as the glass transition temperature of the powder is higher than any environmental temperatures that may occur during normal human use, the powder will remain in a glass state.

Of the various treatment modalities currently in use or under investigation for the delivery of therapeutically effective doses of various growth factor proteins, a wide range of levels of invasiveness are involved. At the opposite end of the invasiveness spectrum, intrapulmonary inhalation therapy, preferably via dry powder formulations, offers significant advantages over previous delivery strategies. As discussed above, formulation and delivery technology has reached a state where a number of therapeutic macromolecules, including insulin, can now be delivered consistently, and at clinically effective levels via inhalation therapy. An added advantage arising from the non-invasive nature of inhalation therapy is that it is particularly attractive in the treatment of chronic heart conditions that require repeated dosing over longer time intervals. The non-invasive nature of the therapy also proves to be of significant advantage in the treatment of acute heart conditions such as the onset of a myocardial infarct. For patients known to be at risk for such a cardiac event, it will be possible to carry a relatively compact dry powder inhalation device so that at the onset of symptoms, the patient can self administer a dose of growth factor that may prove to be significantly effective in reducing the damage induced by the MI, and may eventually prove to constitute the difference between life and death.

Recognizing the large scope of therapies potentially available in the treatment of chronic heart disease, it is therefore an aspect of the present invention to provide a systematic, multi-tiered therapeutic approach to the administration of specific variants of FGF, VEGF and related growth factor proteins, and/or gene therapy. This approach must, of necessity, recognize the relative invasiveness of different treatment modalities, and the likelihood of repeated recourse to such treatment procedures.

The subparts of the specific growth factor formulation of the present invention can be administered simultaneously or in succession. That is to say, in the first case, they are administered by means of a single formulation which contains at least two of the active ingredients and to which the usual excipients and/or coadjuvants known in the art have optionally been added; alternatively, the two active ingredients may be administered sequentially, namely, by means of two different formulations, one containing at least one of the following: FGF1 and FGF2, and the other containing at least one of the following: VEGF, VEGFA and VEGF165.

Accordingly, using technology and techniques readily available to one of ordinary skill in the pharmaceutical formulation arts, it is possible to formulate a composition comprising at least one of the following: FGF1 and FGF2, and also at least one of the following: VEGF, VEGFA and VEGF165, suitable for delivery by oral inhalation, preferably in a dry powder form, or intravenous injection. The preferred concentration range for the growth factor formulation is 20 μg to 30 mg. The preferred dosing schedule for the growth factor formulation by inhalation therapy is to have 2 inhalations 5 minutes apart twice daily for a period of seven days. The preferred dosing schedule for the growth factor formulation by intravenous injection is to have one injection daily for a period of seven days. A preferred method of treatment for mobilization of stem cell is to inject intravenously 30 mg of the growth factor formulation, followed by oral inhalation using a dosing schedule of 2 inhalations 5 minutes apart twice daily for a period of seven days. The amount of the growth factor formulation used for oral inhalation is 4 mg.

The preferred cell for use in cell therapy is the peripheral blood stem cell (PBSC). These are cells that are isolated from the peripheral blood from either the patient or from an HLA-matched donor. PBSC can be collected without the use of general anesthesia, and the procedure is usually performed on an outpatient basis with little or no discomfort during, or after, the collection. Most importantly, more stem cells can often be collected from the peripheral blood than from the bone marrow.

The PBSC are preferably isolated from the peripheral blood of an individual through a process known as apheresis. The PBSC may be further purified by using fluorescence activated cell sorting or density gradient centrifugation. The PBSC are then stored for future use or immediately injected into a patient. The patient may be the same individual whose blood had been harvested or an HLA-matched individual.

The following examples are presented to provide a more complete understanding of the invention. The specific techniques, conditions, materials, proportions and reported data set forth to illustrate the principles and practice of the invention are exemplary and should not be construed as limiting the scope of the invention.

EXAMPLE 1

Intracoronary Injection of FGF-2 in the Treatment of Severe Ischemic Heart Disease: A Maximally Tolerated Dose Study Patient selection. The study was conducted at two centers, the Beth Israel Deaconess Medical Center (Boston, Mass.) and Emory University Hospital (Atlanta, Ga.), and patients were enrolled between December 1997 and July 1998. The study was approved by the Institutional Review Boards at both hospitals. The inclusion criteria selected for patents with advanced CAD with inducible ischemia and who were considered to be suboptimal candidates for either PTCA or CABG. Patients were excluded from the study if they had any of the following criteria: uncompensated congestive heart failure or an ejection fraction<20%; a myocardial infarction within three months; new onset of angina or unstable angina within three weeks; PTCA, CABG, stroke or transient ischemic attack within six months; uncontrolled hemodynamically significant arrhythmias; critical valvular disease; restrictive or hypertrophic cardiomyopathy; arteriovenous malformations; proliferative retinopathy, retinal vein occlusion, or macular edema; renal insufficiency (creatinine clearance<80 ml/min by 24-h urine collection); vasculitis or chronic immunosuppressive therapy; or any malignancy within the past 10 years (except for curatively treated nonmelanoma skin cancer). Patients with diabetes mellitus were eligible if they had no proliferative retinopathy or severe nonproliferative retinopathy, and no microalbuminuria.

Patient population. Fifty-two patients met all eligibility criteria and received a single IC infusion of rFGF-2. The mean age was 60.8.+−.10.1 years (range 41 to 80) and 2 of 52 patients were women. Six patients (11%) had diabetes mellitus and 31 patients (60%) had elevated cholesterol (serum cholesterol>200 mg/dl). Forty-three patients (83%) had a history of at least one prior CABG. The mean ejection fraction (evaluated by MR imaging) was 51.4.+−.12.0% (range 20% to 73%). Sixty-nine percent of patients had NYHA class II or III symptoms of congestive heart failure.

Study design. This was an open-label interpatient dose escalation study. The initial dose of 0.33 g/kg was escalated over eight sequential groups to 48 g/kg IC. At least four patients were studied at each dose. If no patient experienced dose-limiting toxicity as defined by the protocol within six days, the dose was escalated; if one patient experienced dose-limiting toxicity, an additional four patients were studied at that dose. The MTD was defined as the dose tolerated by 9 of 10 patients.

Study procedures. After providing informed consent and meeting all eligibility criteria, patients underwent baseline evaluations that included a complete medical history and physical examination, an ophthalmologic examination with fundus photography read by a core laboratory using the Early Treatment Diabetic Retinopathy score (ETDRS), an exercise tolerance test (ETT), a Seattle Angina Questionnaire (SAQ), and nuclear and MRI cardiac scans. Measurement of initial health status allowed the use of change in scores, thus adjusting for differences in baseline health. Self-administration was used instead of telephone interview to minimize data collection bias.

On day 1, patients underwent right and left heart catheterization and coronary angiography. If the coronary anatomy was not amenable to PTCA or CABG, recombinant FGF-2 (rFGF-2, Chiron Corporation, Emeryville, Calif.) was infused with a Baxter pump through diagnostic catheters into two major conduits of myocardial blood supply over 20 min (10 min in each vessel) with continuous monitoring of systemic blood pressure and right atrial and pulmonary capillary wedge pressures, and cardiac output. In occasional patients the entire dose was infused into a single vessel that was believed to be the major source of blood supply. Prior to initiation of rFGF-2 infusion, normal saline was administered intravenously (i.v.), if required, to ensure mean pulmonary capillary wedge pressure>12 mm Hg. Heparin (40 U/kg) was administered i.v. more than 10 min before rFGF-2. The volume of infusion varied with dose and the patient's weight, ranging from 10 ml at lower does to 40 ml at higher doses.

The right heart (Swan-Ganz) catheter was left in place for 7 h following drug infusion to monitor filling pressures and cardiac output. Patients were monitored with full-disclosure telemetry for 24 h following rFGF-2 administration. Patients were discharged 24 h after study drug infusion and clinical follow-up visits were performed at days 6, 15, 29, 57, 180 and 360. Quality of life was assessed using the Seattle Angina Questionnaire at baseline and days 57 and 180. ETT's were obtained at days 29, 57 and 180. Exercise stressed nuclear perfusion scans (rest thallium/stress .sup.99m Tc-sestamibi) and resting cardiac magnetic resonance scans were performed at days 29, 57 and 180.

Preliminary Efficacy of RFGF-2 Therapy. Although the small sample size and the absence of a control group preclude any definitive conclusions regarding efficacy, several findings suggest potential clinical benefits of intracoronary rFGF-2 administration. In particular, quality of life, as assessed by the SAQ, improved in treated patients at day 57 compared with baseline, and this improvement was sustained for six months. The magnitude of improvements in the five SAQ scales was similar to that seen following PTCA and CABG in patients with ischemic heart disease. There was also a significant improvement in exercise capacity, as measured by exercise treadmill testing, seen at days 57 and 180. Of note, there was minimal improvement at day 29. The late occurrence of improvement in exercise testing is in keeping with the assumed time course of coronary angiogenesis. However, the absence of a dose response tempers the preliminary efficacy seen in this study.

In addition, to these subjective measures of clinical status, resting MR imaging was performed to assess left ventricular function and myocardial perfusion. Using this approach, we detected no difference in overall left ventricular ejection fraction at any time during the study. However, there was a significant improvement in systolic thickening of the target wall at day 29, which was maintained at six months, and was paralleled by a significant reduction in the size of the ischemic myocardium as assessed by blood arrival imaging. Although cardiac MR imaging is considered the "gold standard" for evaluation of left ventricular function, its application to clinical trials in coronary disease is very limited. Similarly, despite recent advances in MR-based perfusion assessment of the myocardium, there has been no substantial clinical experience with this imaging modality. Prior animal studies have documented improvement in MR-assessed parameters of left ventricular function in the setting of angiogenic growth factor therapy. In addition, the newly developed variation of MR perfusion imaging that relies on generation of space-time maps proved capable of detecting changes in coronary perfusion in a pig ameroid model and proved capable of detecting improved regional myocardial perfusion in patients treated with epicardially administered sustained release FGF-2.

A fundamental question pertaining to IC delivery is how a drug with a relatively short plasma half-life can promote a relatively long-term process such as new collateral formation. One possible explanation is that first-pass extraction at the desired site of action is the primary determinant of FGF-2 biological effect. Although such extraction certainly occurs, animal studies demonstrated that <1% of .sup.125 I-FGF-2 administered using the intracoronary route is deposited in the myocardium at 1 h and much less remains at 24 h. Although there is enhanced first-pass FGF-2 uptake in ischemic compared with normal myocardium, presumably due to increased expression of cellular heparin sulfates and FGF receptor-1, myocardial levels fall to very low levels at 24 h in both normal and ischemic regions of the heart. One speculative explanation is that this transient accumulation of FGF-2 in the ischemic myocardium sets in motion a self-amplifying cascade that includes the influx and endothelial adhesion of monocytes/macrophages and stimulation of expression of VEGF and other angiogenic cytokines, which may lead to prolonged and sustained action.

Safety Assessment. The safety of intracoronary rFGF-2 was assessed through clinical observations, electrocardiography, hemodynamic monitoring, hematologic and serum chemistry profiles, development of anti-rFGF-2 antibodies, detailed ophthalmological exams with fundus photography and assessment of renal function by determination of creatinine clearance and proteinuria using 24-h urine collection. Dose-limiting toxicity was predefined as a persistent (>10 min) drop in systolic blood pressure by >50 mm Hg, change in heart rate to >120/min or to <50/min, new clinically significant arrhythmia, new ischemic symptoms or ECG changes, new congestive heart failure, deterioration in renal function or any other serious adverse events.

Clinical follow-up and safety assessment. Clinical follow-up of at least six months was obtained on all patients. A total of 30 serious adverse events were reported in 22 patients. There was no apparent relationship between increasing dose of rFGF-2 and serious adverse events.

Four patients died. Two deaths were sudden and occurred 22 days (0.65 g/kg dose, EF 30%) and 114 days (48 g/kg dose, EF 22%) after rFGF-2 infusion. One death was due to complications of cardiac transplantation and one death was due to complications of large-cell lymphoma. Both instances of sudden death occurred in patients with reduced left ventricular function (22% and 30%). Although sudden death may be part of the natural history of their disease, potential partial revascularization in these patients may have induced ventricular tachyarrhythmias. The diagnosis of large-cell non-Hodgkin's lymphoma 10 days after rFGF-2 infusion most likely reflected the presence of disease that antedated IC rFGF-2 administration. Nevertheless, it is possible that rFGF-2 may have exacerbated the lymphoma course.

One patient (2 g/kg) died 72 days after rFGF-2 infusion from complications of cardiac transplantation after sustaining several myocardial infarctions beginning four days after drug infusion. One patient with preexisting lymphadenopathy (6 g/kg) died at 62 days from septic complications of large-cell lymphoma, which was diagnosed at 10 days after dosing. In retrospect, the lymphoma most likely predated rFGF-2 infusion. One additional patient was diagnosed with metastatic adenocarcinoma to the liver at day 431.

Four patients had non-Q-wave myocardial infarctions at days 5 (2 g/kg dose group), 68 (6 g/kg), 132 (0.33 g/kg) and 146 (48 g/kg). Four patients had revascularization procedures (CABC and aortic value replacement in one patient at day 68 [6 g/kg] and PTCA in three patients at day 100 (0.33 g/kg), 290 [24 g/kg], and 223 [48 g/kg]). One patient developed atrial fibrillation at day 37. The most commonly reported (>10% of patients) adverse events were asthenia (19%), hypotension (15%), dyspnea (13%), insomnia (13%), angina (12%) and palpitations (12%). Of these asthenia, hypotension, insomnia, and dyspnea were more common at higher doses. No patients withdrew from the study because of adverse events. Transient leukocytosis was observed in half the patients at .gtoreq.24 g/kg. Fluctuations in renal function occurred but were transient and not dose related. Proteinuria (>250 mg/24 h) occurred in four patients (7.8%). Ophthalmological exams with fundus photography at baseline and day 57 were available for 45 patients; seven patients lacked wither baseline or 57-day assessments. Forty patients (89%) showed no change from baseline, two patients improved by two ETDRS grades and three patients worsened by two grades (0.65, 2.0 and 36.0 g/kg groups).

Safety and Tolerability of RFGF-2 Administration. The ability to administer fairly high does of rFGF-2 (up to 36 g/kg IC) without significant hemodynamic effects is somewhat surprising given prior reports of severe FGF-2-induced hypotension and the known capacity of this cytokine to stimulate NO release and induce arteriolar vasodilation. Hypotension was dose-related and dose limiting, but was rapidly correctable by IV fluids. This finding is in sharp contrast to clinical experience with another NO-releasing growth factor, VeGF-A$_{.sub.165}$, where profound hypotension limits systemic administration. This difference in part may be attributable to careful hemodynamic monitoring in these patients and a requirement for adequate pressure (>12 mm Hg) before initiation of rFGF-2 infusion.

Preclinical studies as well as limited clinical experience to date suggested that renal insufficiency due to membranous nephropathy accompanied by proteinuria may be the most significant long-term side effect of FGF-2 administration. In this small trial, only four instances of proteinuria were observed. In should be noted, however, that all patients studied had normal renal function at baseline.

Additional serious side effects included the occurrence of non-Q-wave myocardial infarction in four patients, raising the possibility that FGF-2 may have promoted growth, or destabilization of coronary plaque owing to its broad-spectrum mitogenicity and chemotactic activity. The latter possibility may be particularly relevant given the ability of FGFs to induce angiogenesis in vasa vasorum and the association between plaque angiogenesis and its growth and stability. Although these concerns are certainly worrisome, in the absence of a control group casual relationships cannot be confirmed or discounted.

Statistical methods. Data are pooled for all dose groups. Baseline characteristics and acute hemodynamic parameters are expressed as mean.+−.standard deviation. Efficacy variables were analyzed using a linear mixed effects model with an unstructured covariance assumption for the repeated measurements, fit using the restricted maximum likelihood method. Model-based estimates of the means.+−.standard errors (SEM) are presented. An overall F-test for equality across all time points was conducted first. If this initial test was statistically significant, pairwise t tests to compare baseline with each on-study time point were performed at the nominal a-level. All reported p-values are two-sided, and a p-value<0.05 was considered statistically significant.

Magnetic resonance (MR) imaging. Magnetic resonance (MR) imaging was performed at baseline and days 29, 57 and 180 in the body coil of a 1.5 T whole-body Siemens Vision or Philips NT system. Functional imaging was performed during breath-hold using shared-center FLASH or multishot echoplanar imaging in each of the three mutually perpendicular standard views, producing 16-24 sequential image frames each, collected over approximately 12 heartbeats to measure regional wall systolic thickening. MR blood arrival imaging was assessed as previously described. A series of four inversion recovery images was obtained with the inversion time (TI) adjusted to minimize signal intensity from myocardium. Using the best TI for nulling myocardial signal, a series of concurrent parallel images were acquired in diastole during breathhold, at baseline and after the bolus injection of contrast media (0.05 mmol/kg gadodiamide). Measurement of the timing of half-maximum signal arriving in the different parts of the myocardium demonstrated the existence of several distinct regions, including normal myocardium and areas exhibiting delayed contrast arrival (ischemic zones). For each scan, a pace-time map demonstrating distribution of contrast signal density over the left ventricular wall as a function of time was created. The extent of the territory demonstrating delayed arrival of contrast, defined as >1-s delay of contrast density reaching its 50% maximum value reflecting the most severely hypoperfused part of the myocardium, was then calculated and expressed ads percent of the total left ventricular myocardial area. MR analysis was performed by a core lab blinded to rFGF-2 dose assignment and to study sequence.

Quality of life assessment. There were significant improvements in all five scales of the Seattle Angina Questionnaire at days 57 and 180, as compared with baseline. In particular, angina frequency score increased (denoting improvement) from 39.8.+−.3.8 at baseline to 68.8.+−.4.0 (p<0.001) at day 57 and 64.7.+−.4.5 at day 180 (p<0.001), overall p<0.001. Exertional capacity score increased from 49.2.+−.2.8 at baseline to 64.5.+−.3.1 at day 57 (p<0.001) and 73.0.+−.3.8 at day 180 (p<0.001), overall p<0.001.

Exercise treadmill testing. A subset of patients with matching baseline and follow-up exercise treadmill protocols was selected for analysis. Among this group, the mean exercise time improved from 510.+−.24 s at baseline (n=35) to 561.+−.26 s at day 29 (n=28; p=0.023), 609.+−.26 s at day 57 (n=31; p<0.001), and 633.+−.24 s at day 180 (n=23; p<0.001).

Left ventricular function assessment. Magnetic resonance imaging was performed in 51 patients at baseline and was repeated at days 29 (n=47), 57 (n=45) and 180 (n=31) to assess resting left ventricular ejection fraction, regional wall motion, and myocardial contrast arrival. There was a small improvement in overall left ventricular ejection fraction over the course of the study (baseline 51.4.+−.1.7%, day 29: 54.2.+−.1.7% [p=0.02], day 57: 55.2.+−.1.9% {p=0.003}, day 180: 57.2.+−.1.7% [p<0.001], overall p=0.002). The hypoperfused target area was selected for resting regional left ventricular wall motion analysis. Systolic thickening of this area (target wall) and normal wall were measured using a semiautomated quantification algorithm of short-axis MR images. Resting normal wall systolic thickening was 46.1.+−.1.6% at baseline and did not change significantly throughout the study duration (p=0.16). Resting target wall thickening was significantly lower than normal wall thickening at baseline (34.0.+−.1.7% vs. 46.1.+−.1.6%, p<0.001). Target wall thickening significantly improved at days 29, 57, and 180 as compared to baseline [baseline: 34.+−.1.7%, day 29: 38.7.+−.1.9% (p=0.006), day 57: 41.4.+−.1.9% (p<0.001), and day 180: 42.0.+−.2.3% (p<0.001), overall p=0.001].

Myocardial perfusion assessment. Myocardial perfusion was assessed using MR imaging. The mean size of the delayed contrast arrival zone was 15.4.+−.0.8% of the left ventricle at baseline and was similar to the global left ventricular extent of ischemia determined by nuclear perfusion imaging (17.3.+−.1.8%). The size of the myocardial area demonstrating delayed contrast arrival was significantly reduced from baseline (15.4.+−.0.8%) at day 29 (9.0.+−

.0.6%, p<0.001), day 57 (5.6.+−.0.7%, p<0.001) and day 180 (4.9.+−.0.8%, p<0.001), overall p<0.001.

There was no correlation between the dose and the various efficacy parameters studied.

EXAMPLE 2

Safety and Efficacy of a Single Intrapericardial Injection of FGF-2 in a Porcine Model of Chronic Myocardial Ischemia Chronic Myocardial Ischemia Model. Yorkshire pigs of either sex weighing 15 to 18 kg (5-6 weeks old) were anesthetized with intramuscular (i.m.) ketamine (10 mg/kg) and halothane by inhalation. A right popliteal cut-down was performed and a 4 French arterial catheter was inserted for blood sampling and pressure monitoring. Left thoracotomy was performed through the 4th intercostal space. The pericardium was opened, and an ameroid constrictor of 2.5 mm i.d. (matched to the diameter of the artery) was placed around the left circumflex coronary artery (LCX). The pericardium was closed using 6-0 Prolene suture, (J&J Ethicon, Cincinnati, Ohio) and the chest was closed. A single dose of i.v. cefazolin (70 mg/kg) was given, and i.m. narcotic analgesics were administered as needed. Animals then were allowed to recover for 3 weeks (time sufficient for ameroid closure) before growth factor delivery. The treatment of animals was based on the National Institutes of Health guidelines, and the protocol was approved by the Institutional Animal Care and Utilization Committee of the Beth Israel Deaconess Medical Center.

Growth Factor Delivery. Three weeks after ameroid placement, animals were anesthetized with i.m. ketamine (10 mg/kg) and isoflurane by inhalation. A right femoral cut-down was performed and an 8 French arterial sheath was inserted for blood sampling, pressure monitoring, and left heart catheterization. Coronary angiography was then performed in multiple views using a 7 French JR4 diagnostic catheter (Cordis, Miami, Fla.) to confirm LCX occlusion and to assess the extent of collateral circulation in the LCX distribution ("collateral index"). After LCX occlusion was documented, percutaneous subxyphoid pericardial access was undertaken. With the animals in the supine position, the epigastric area was prepped and draped. An epidural introducer needle (Tuohy-17) was advanced gently under fluoroscopic guidance with a continuous positive pressure of 20 to 30 mm Hg. Entry into the pericardial space was confirmed by the injection of 1 ml of diluted contrast. A soft floppy-tipped guidewire was then advanced into the pericardial space and the needle was exchanged for a 4 French infusion catheter.

The animals were randomized to one of five treatment groups:
1. Control: intrapericardial saline (n=10).
2. Heparin: intrapericardial heparin (3 mg, n=9).
3. FGF-2 30 .mu.g: intrapericardial FGF-2 (30 .mu.g)+3 mg of heparin (n=10).
4. FGF-2 200 .mu.g: intrapericardial FGF-2 (200 .mu.g)+3 mg of heparin (n=10).
5. FGF-2 2 mg: intrapericardial FGF-2 (2 mg)+3 mg of heparin (n=10).

The infusate was diluted to 10 ml with saline and infused over 5 min with continuous electrocardiographic and pressure monitoring. The catheter was withdrawn, and a set of colored microspheres (blue) was injected into the left atrium to obtain baseline (pretreatment) myocardial blood flow. Finally, a magnetic resonance study was carried out to obtain quantitative measures of global and regional left ventricular function [ejection fraction (EF) and radial wall motion] and assessment of perfusion using myocardial contrast density mapping. The animals then were allowed to recover for 4 weeks.

Final Study. Four weeks after intrapericardial agent administration, all animals underwent final evaluation. Pigs were anesthetized with i.m. ketamine (10 mg/kg) and isoflurane by inhalation. A left femoral cut-down was performed and an 8 French arterial sheath was inserted for blood sampling, pressure monitoring, and left heart catheterization. Coronary angiography was performed again in multiple views. A second magnetic resonance study was carried out for global and regional left ventricular function and myocardial perfusion.

Myocardial blood flow was determined using colored microspheres at rest (yellow) and after maximal coronary vasodilation with i.v. adenosine (white). Animals then were euthanized under anesthesia and the heart was obtained for additional analysis. In addition, a detailed macroscopic and histologic postmortem examination was carried out on three animals in each group.

A total of 56 animals survived ameroid placement around the LCX coronary artery with resultant total LCX occlusion at 3 weeks. Seven animals died after being randomized to a treatment group. Six of these seven animals died within 72 h of intrapericardial agent delivery. Of the seven animals deaths, two animals died of hypoxemia (one control animal and one FGF-2 30 .mu.g animal) due to failure of mechanical ventilation before growth factor delivery, four animals died during MRI (three animals died before growth factor delivery and one after pericardial access and delivery, with two animals randomized to the 200 .mu.g FGF-2 group and two animals in the control group), and one animal died of unknown cause 26 days after growth factor delivery (heparin group). The remaining 49 animals were randomized to each of five treatment groups with 10 animals in each of the FGF-2 and saline control groups and 9 animals in the heparin group. There were no significant hemodynamic effects of intrapericardial FGF-2 administration at any dose; no changes in blood pressure, heart rate, or left atrial pressure were observed with drug administration.

Angiographic Analysis. Coronary angiography was performed in multiple views (right anterior oblique, anteroposterior, and left anterior oblique views for the left coronary artery; right anterior oblique and left anterior oblique for the right coronary artery). Evaluation of angiographic collateral density was performed by two independent angiographers blinded to treatment assignment. Differences in interpretations were resolved by a third angiographer. The collateral index was assessed for left-to-left and right-to-left collaterals using a 4-point scale (0, no visible collateral vessels; 1, faint filling of side branches of the main epicardial vessel without filling the main vessel; 2, partial filling of the main epicardial vessel; and 3, complete filling of the main vessel).

Coronary Angiography Baseline right and left coronary angiography was available on all 49 animals and final angiography was available on 47 animals. Left-to-left collaterals and right-to-left collaterals were measured (collateral index). The extent of left-to-left collaterals pre- (3 weeks after ameroid placement) and post-treatment (7 weeks after ameroid placement) in all groups shows a significant improvement over baseline in the collateral index of all three FGF-2 treatment groups (30 .mu.g, 200 .mu.g, and 2 mg) with no significant improvement noted in control or heparin-treated animals. Only animals in the FGF-2 2 mg group displayed a trend toward improvement in right-to-left collateral index (collateral index increased by 0.67.+−.0.87, P=0.06).

Myocardial Blood Flow. Colored microspheres (15.+−.0.1 .mu.m diameter; Triton Technology Inc., San Diego, Calif.) were used to determine coronary blood flow before treatment initiation (blue) and at the time of final study (yellow and white). For determination of coronary flow at 3 and 7 weeks after ameroid placement, an angiographic JR4 catheter was advanced into the left ventricle and manipulated to engage the left atrium outflow by slow counterclockwise rotation of the catheter; catheter position was verified by contrast injection into the left atrium. In addition, mean left atrial pressure was recorded. A set of microspheres (6.times.10.sup.6) was diluted in 10 ml of saline and injected into the left atrium over 30 s. Reference blood samples were withdrawn by using a syringe pump at a constant rate of 5 ml/min through the femoral artery. At the time of final study, coronary flow was measured at rest and after maximal vasodilation (achieved with the injection of i.v. adenosine, 1.25 mg/kg). After study completion, the heart was excised and regional myocardial blood flow was determined. The heart was excised and a 1-cm midtransverse slice was sectioned and cut into eight segments. The tissue samples and the reference blood samples were digested in an 8 M KOH/2% Tween 80 solution and microspheres were collected using a vacuum filter. Dyes from microspheres were extracted using dimethyl formamide. Samples were then analyzed in a spectrophotometer (HP 8452 A; Hewlett Packard, Palo Alto, Calif.).

Regional blood flow was calculated from optical absorbance (AU) measurements corrected by tissue weight as follows:

Flow to sample (ml/min/g)=(*AU*/sample)(reference withdrawal rate)/*wt*./(*AU*/reference sample)

To evaluate further the angiogenic potential of intrapericardial FGF-2 in chronic myocardial ischemia, regional myocardial blood flow was measured at different time points using colored microspheres. Three weeks after implantation of ameroid occluders, at the time of intrapericardial drug delivery, resting myocardial blood flow in the LCX territory was similar in all treatment groups [baseline coronary flow (ml/min/g): 1.00.+−.0.31 in controls and 0.97.+−.0.23 in heparin-treated animals versus 0.92.+−.0.08 in the 30 .mu.g FGF-2 group, 0.99.+−.0.15 in the 200 .mu.g FGF-2 group, and 1.10.+−.0.14 in the 2 mg FGF-2 group, P=0.94] and was significantly lower than flow in the LAD territory (LCX flow: 1.00.+−.0.35 ml/min/g versus LAD flow: 1.43.+−.0.43 ml/min/g, P<0.0001). Four weeks after intrapericardial drug delivery, LCX flow was significantly higher in FGF-2-treated animals than in controls and heparin-treated animals (ANOVA P=0.002). At the time of the final study, coronary flow (ml/min/g) was 1.05.+−.0.21 in controls (P=0.7 compared with baseline) and 1.09.+−.0.13 in the heparin group (P=0.19 compared with baseline and P=0.6 compared with controls) versus 1.31.+−.0.12 in the 30 .mu.g FGF-2 group (P=0.0001 compared with baseline and P=0.004 compared with controls), 1.25.+−.0.15 in the 200 .mu.g FGF-2 group (P=0.002 compared with baseline and P=0.03 compared with controls), and 1.32.+−.0.16 in the 2 mg FGF-2 group (P=0.004 compared with baseline and P=0.005 compared with controls).

MRI. MRI was performed on all animals at the time of treatment initiation and at the time of final study. MRI was carried out in the body coil of a 1.5 Tesla whole body Siemens Vision system (Iselin, N.J.) as previously described. The following measurements were performed:

a. Determination of resting left ventricular EF (%).
b. Analysis of regional wall motion using percentage of wall thickening.
c. Determination of the extent of coronary perfusion in the LCX collateral-dependent territory compared with normal myocardium by measuring gadodiamide-enhanced signal intensity in different parts of the left ventricular wall and generating a space-time map of myocardial perfusion). The space-time maps allow the measurement of the extent of the ischemic zone.

MRI was available on 44 animals (8 in the control group; 9 in the heparin group; and 9 in each of the 30 .mu.g, 200 .mu.g, and 2 mg FGF-2 groups). In five animals, MRI was not performed due to temporary technical problems with the MRI system at the time of the final study. The porcine ameroid occlusion model is associated with the development of small areas of left ventricular myocardial necrosis in most animals.

Global Left Ventricular Function. To assess the functional significance of FGF-2-mediated improvement in myocardial blood flow, MRI was used to assess global and regional left ventricular function in all study animals. There were no significant differences in global left ventricular function among the five groups (EF was 44.1.+−.6.4% in controls and 44.2.+−.6.8% in heparin-treated animals versus 47.07.+−.2.68 in the 30 .mu.g FGF-2 group, 45.52.+−.3.41 in the 200 mg FGF-2 group, and 47.98.+−.3.14 in the 2 mg FGF-2 group; ANOVA, P=0.35).

Regional Left Ventricular Function. Measurement of regional wall thickening in the LAD (normal territory) and LCX (ischemic) territories was used to assess regional left ventricular function (FIG. 2). LAD (normal) wall thickening was similar in all groups (ANOVA, P=0.86). FGF-2-treated animals had improved regional wall thickening in the LCX (ischemic) territory compared with controls and heparin-treated animals [FIG. 2; LCX wall thickening (%): controls, 33.58.+−.9.91; heparin, 32.64.+−.13.45 (P=0.87 compared with controls); FGF-2 30 .mu.g, 42.12.+−.6.43 (P=0.05 compared with controls); FGF-2 200 .mu.g, 43.23.+−.6.41 (P=0.03 compared with controls); and FGF-2 2 mg, 47.14.+−.3.64 (P=0.002 compared with controls); ANOVA, P=0.003]. Linear regression (assuming heparin results in no significant FGF-2 release) revealed a dose-dependent improvement in LCX wall thickening in the FGF-2-treated animals (y=37.6.+−.0.005x, P=0.007).

Figure 3:
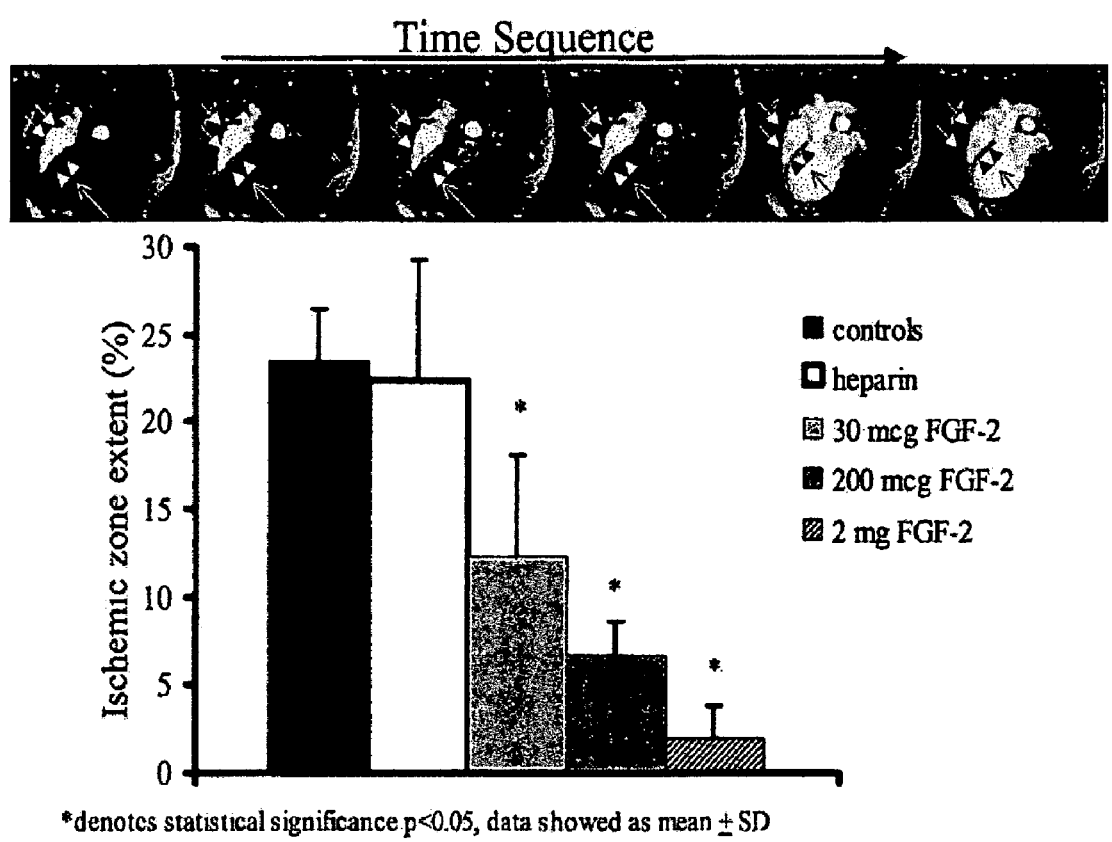
FIG. 3 is an illustration of, at top, MRI perfusion images of the left ventricle and, at bottom, the ischemic zone extent in all groups of test animals.

Myocardial Perfusion. First-pass inversion-recovery turbo-FLASH MRI was used to generate a space-time map of myocardial perfusion (FIG. 3 top). Three distinct zones are observed that are characterized by either prompt signal appearance, failure of the signal to increase in intensity (infarction), or delayed signal appearance (delayed contrast arrival or ischemic zone). On the basis of contrast density data, a two-dimensional map of contrast intensity versus time was generated and was used to measure the size of the myocardial segments showing impaired (delayed) contrast arrival. FIG. 3 (bottom) depicts the extent of the ischemic zone of contrast in the five groups. FGF-2 induced a dose-dependent reduction in the extent of the ischemic zone, indicating achievement of better myocardial perfusion in the FGF-2 treatment groups [FIG. 3 bottom; ischemic zone (% of left ventricle): controls, 23.54.+−.2.84; heparin, 22.41.+−.6.85 (P=0.66 compared with controls); FGF-2 30 .mu.g, 12.27.+−.5.82 (P=0.0001 compared with controls); FGF-2 200 .mu.g, 6.63.+−.1.97 (P<0.0001 compared with controls); and FGF-2 2 mg, 2.02.+−.1.83 (P<0.0001 compared with controls); ANOVA, P<0.0001; linear regression y=16.7−0.008x, P<0.00011].

Histopathologic Analysis and Toxicology. Complete autopsies were performed on 15 animals (3 animals in each group). Tissues obtained from the liver, lung, kidney, spleen, eye, bone marrow, and stomach were formalin-fixed and paraffin-embedded. Sections (5 .mu.m) were obtained from all tissue samples, stained with hematoxylin/eosin, and examined microscopically. In addition, tissue samples were obtained from pericardium, epicardial coronary artery, and myocardium in the left anterior descending coronary artery (LAD) distribution (normal) and LCX distribution (ischemic). Sections were stained with hematoxylin/eosin as well as by the Verhoeff-Van Gieson method for collagen and elastin. Complete serum chemistry and hematology studies were performed at 3 and 7 weeks in all animals.

There were no treatment-related macroscopic or microscopic findings in any of the organs examined. One animal had a single kidney present. there was focal to diffuse minimal thickening of the pericardium in all FGF-2 treatment groups, which was due to a slight increase in connective tissue (fibrosis). There were minimal to mild chronic inflammatory cell infiltrates accompanied by focal or multifocal mineralization in all FGF-2 treatment groups. Increased vascularity was noted in the pericardium of two of three animals examined in the 200 .mu.g FGF-2 group and one of three animals examined in the 2 mg FGF-2 group, but was not observed in the control, heparin, or 30 .mu.g FGF-2 groups (FIG. 4B). In addition, the LAD and LCX in these animals were examined and they showed no evidence of intimal hyperplasia.

Finally, there was an increase in vascularity of the epicardium and myocardium in all animals from the 30 .mu.g, 200 .mu.g, and 2 mg FGF-2 groups, but not in controls or heparin-treated animals. Sections from the LCX but not the LAD distribution in all FGF-2 treatment groups showed an increase in the number of capillaries. Many of these small blood vessels were lined by endothelial cells that had large hyperchromatic nuclei, suggestive of new vascular in-growth (FIG. 4A). FGF-2 treatment did not result in any significant abnormalities in serum chemistries, hematology, and coagulation studies.

EXAMPLE 3

Nonmitogenic Effects of Administration of FGF-2 in Acute Myocardial Ischemia and Reperfusion in a Murine Model To determine whether nonmitogenic effects of FGF-2 could be beneficial to the heart during acute myocardial ischemia and reperfusion, FGF-2 is administered in a murine model of myocardial stunning. The advantages of this mouse model are well-defined markers of ischemia-reperfusion injury, including ischemic contracture, alteration in calcium homeostasis, and prolonged ventricular dysfunction, occurring within a time window too short to activate the mitogenic properties of FGF-2. Transgenic mouse hearts deficient in the expression of the inducible isoform of NOS (NOS2−/−) are used to further investigate the coupling of FGF-2 and NO during acute myocardial ischemia and reperfusion.

Stunning. Myocardial stunning is the phenomenon whereby an ischemic insult interferes with normal cardiac function, cellular processes, and ultrastructure for prolonged periods. Numerous mechanisms of myocardial stunning have been proposed, the most probable of which include generation of oxygen-derived free radicals, metabolic impairment, and calcium overload. Recently, a number of pharmacological agents and physiological manipulations have been shown to induce early or late ischemic preconditioning, a state characterized by reduced susceptibility to postischemic decline in myocardial function. In particular, FGF-2 has been demonstrated to improve myocardial function in the setting of acute myocardial ischemia both in vivo and in isolated rat heart studies. The well-known angiogenic effects of FGF-2, however, occur too gradually to be relevant in such settings. The purpose of this study, therefore, is to study the potential role of NO release in FGF-2-mediated cardioprotection and to define the NOS isoform responsible for FGF-2-induced NO release.

Fifteen minutes of global ischemia followed by twenty minutes of reperfusion results in prolonged ventricular dysfunction characterized by reduced levels of LVP generation as well as significant decreases in dP/dt.sub.max and dP/dt.sub.min. Pretreatment with rFGF-2 significantly improves the extent of recovery of LVP compared with control (untreated) hearts (83.+−.5 vs. 61.+−.6%) and equally significant preservation of dP/dt.sub.max and dP/dt.sub.min (86.+−.3 vs. 65.+−.6% and 85.+−.5 vs. 60.+−.5%, respectively. Stunning in hearts perfused with either NOS inhibitor by itself is not different from that in control hearts. Functional recovery of LVP in untreated control hearts (61.+−.6%) is not significantly different from that in hearts perfused with either L-NAME alone (59.+−.9%) or L-NIL alone (57.+−.6%). Depression of dP/dt.sub.max and dP/dt.sub.min (65.+−.6 and 60.+−.5%, respectively) in untreated hearts is similar to that in hearts perfused with L-NAME alone (60.+−.9 and 55.+−.8%, respectively) and hearts perfused with L-NIL alone (57.+−.9 and 67.+−.4%, respectively).

Unlike initial pretreatment with rFGF-2, addition of the growth factor to the coronary perfusate after the onset of ischemia, immediately before reperfusion, does not improve LV function 20 min after reperfusion (LVP 60.+−.4%, dP/dt.sub.max 62.+−.4%, and dP/dt.sub.min 58.+−.4%, all P-NS vs. control). As in the case of acute ischemic changes, pretreatment with either L-NAME or L-NIL leads to a complete inhibition of rFGF-2 effects (FIGS. 2 and 3).

Isolated Heart Preparation. Hearts are excised from adult C57/BL6 mice of either sex that have been anesthetized and heparinized (500 U/100 g body wt). The aorta is slipped over a 20-gauge blunt-tipped stainless steel needle through which oxygenated (95% O.sub.2-5% CO.sub.2) Krebs-Henseleit (KH) buffer (in mM: 118.0 NaCl, 4.7 KCl, 1.2 KH.sub.2PO.sub.4, 1.5 CaCl.sub.2, 1.2 MgCl.sub.2, 23.0 Na HCO.sub.3, 10.0 dextrose, and 0.3 EDTA, pH 7.4) is pumped at a rate of .sup.−3 ml/mm. An intraventricular balloon catheter system specially designed for the mouse heart is passed through the mitral annulus into the left ventricle, and the distal end of the balloon catheter is connected to a Statham P23b (Gould, Cleveland, Ohio) transducer to record intraventricular pressure, Left ventricular (LV) pressure recordings are analyzed with regard to LV developed pressure (LVP), LV end-diastolic pressure, peak rate of pressure development (dP/dt.sub.max), time to 90% pressure decline, and peak rate of pressure decline (dP/dt.sub.min).

Ischemia and reperfusion. The hearts are subjected to no-flow ischemia for 15 min. The organ bath is evacuated of its oxygenated solution and refilled with nitrogen-saturated perfusate. Pacing is maintained during ischemia. LV pressure is monitored throughout ischemia and reperfusion. All hearts cease to contract within 3 min. The time for LVP to fall to 10% of baseline (T.sub.LVP10) is measured to quantify differences in LV function during early ischemia. Mean ischemic $Ca_i^{2+}$ is calculated as the mean $Ca_i^{2+}$ recorded from the 2nd through the 14th minute of ischemia. Contracture is defined as an abrupt and sustained rise in intraventricular pressure above 4 mmHg. Contracture time is measured as the time from the onset of ischemia to the onset of contracture. At the end of 15 mm of ischemia, the nitrogen-saturated bath is replaced by the original bath maintained at 30.degree. C. Flow is recommenced. Mean $Ca_i^{2+}$ during early reflow is calculated as the mean of the peaks of $Ca_i^{2+}$ recorded during the 1st minute of reperfusion. After 20 min of reperfusion, $Ca_i^{2+}$ and functional parameters are again measured.

Drugs. Recombinant bovine FGF-2 (rFGF-2) is obtained from Chiron (Sunnyvale, Calif.). $N^G$-nitro-L-arginine methyl ester (L-NAME), an inhibitor of NOS, is obtained from RBI (Natick, Mass.). $L-N^6$-(1-iminoethyl)lysine (L-NIL), a selective inhibitor of NOS2, is obtained from Sigma (St. Louis, Mo.). All studies are conducted at 30.degree. C., and hearts are paced at 6 Hz to minimize consumption of aequorin. After a 15-min equilibrium period, baseline conditions are recorded. Subsequently, hearts are divided into the following perfusion groups: perfusion with KH for 40 min (control, n=10), perfusion with KH for 20 min followed by perfusion with KH plus 1 .mu.g/ml rFGF-2 for 20 min (rFGF-2, n=10), perfusion with KH plus 400 .mu.M L-NAME for 20 min followed by perfusion with KH plus 400 .mu.M L-NAME plus 1 .mu.g/ml rFGF-2 for 20 min (L-NAME+rFGF-2, n=6), and perfusion with KH plus 400 .mu.M L-NIL for 20 min followed by perfusion with KH plus 400 .mu.M L-NIL plus 1.mu.g/ml rFGF-2 for 20 min (L-NIL+rFGF-2, n=5). To test the effect of perfusion with the NOS inhibitors in the absence of rFGF-2, the following two additional perfusion groups are studied: perfusion with KH for 20 min followed by perfusion with KH plus 400 .mu.M L-NAME for 20 min (L-NAME, n=5), and perfusion with KH for 20 min followed by perfusion with KH plus 400 .mu.M L-NIL for 20 min (L-NIL, n=5).

Measurement of Intracellular $Ca^{2+}$ In hearts in which intracellular $Ca^{2+}$ ($Ca_i^{2+}$) is estimated, aequorin is injected into the apex of the heart. Briefly, after the perfusate is modified to contain 0.5 mM $CaCl_2$, 0.6 mM $MgCl_2$, and 20 mM dextrose, 1-3 .mu.l of aequorin are injected with a glass micropipette into a localized region of 2 $mm^2$ at the apex of the heart. The heart is positioned in an organ bath such that the aequorin-loaded region is sup.-2 mm from the bottom of the bath. The $Ca^{2+}$ and $Mg^{2+}$ concentrations of the perfusate are increased to 2.5 mM $Ca^{2+}$ and 1.2 mM $Mg^{2+}$ in a stepwise fashion over a period of 40 min. The entire isolated heart preparation is positioned in a light-tight box for collection of the aequorin light signal. Aequorin luminescence is detected by a photomultiplier tube and recorded as anodal current. For estimation of $Ca_i^{2+}$, Triton X-100 is injected into the coronary perfusate to quickly permeabilize the myocardial cell membranes and expose the remaining active aequorin to saturating $Ca^{2+}$. This resulted in a burst of light, the integral of which approximated the maximum light (L.sub.max) against which light signals of interest (L) provide the fractional luminescence (L/L.sub.max). L/L.sub.max is referred to a calibration equation to estimate $Ca_i^{2+}$.

Myocardial Calcium Homeostasis. Changes in myocardial $Ca_i^{2+}$ are thought to play an important role in ischemia-induced myocardial dysfunction. Therefore, additional experiments are carried out to assess the effect of rFGF-2 administration on myocardial ionized calcium levels. Myocardial $Ca_i^{2+}$ measured at baseline is not different between NOS2+/+ and NOS2-/- hearts, and pretreatment with rFGF-2 has no effect on these levels. Interruption of coronary flow produces abrupt alterations in $Ca_i^{2+}$ in all hearts, with a gradual rise in diastolic and peak $Ca_i^{2+}$ as ischemia progresses. Mean ischemic $Ca_i^{2+}$, $Ca_i^{2+}$ averages from the 2nd through the 14th minute of ischemia, is not affected by rFGF-2 pretreatment and is the same in NOS2+/+ and NOS2-/- hearts. Restoration of coronary flow is followed by a marked increase in myocardial $Ca_i^{2+}$. Neither the extent of this increase nor peak $Ca_i^{2+}$ levels is affected by rFGF-2 administration in NOS2+/+ or NOS2-/- hearts.

Measurement of NO Additional NOS2+/+ (n=5) and NOS2-/- hearts (n=5) are used to measure NO concentration in the coronary effluent using an amperometric sensor (ISO-NO, World Precision Instrument, Sarasota, Fla.). Briefly, after 20 min of perfusion with either vehicle or 1 .mu.g/ml rFGF-2, the electrode is positioned in the effluent to measure the amount of NO released from the coronary sinus. Electrode calibration is performed before each experiment with NO generated from the reaction of S-nitroso-N-acetylpenicillamine (Sigma) with cupric sulfate (Sigma) and acidic solution.

Quantification of NOS Gene Expression To determine NOS2 and NOS3 mRNA levels in FGF-2-treated compared with control hearts, 30 cycles of RT-PCR are performed on equal amounts of total RNA from six control and six rFGF-2-treated hearts using primers corresponding to human NOS3 and NOS2 sequences. For NOS3, primers are as follows: 5' (sense), 5'-CAGTGTCCAACATGCTGCTG-GAAATTG-3' (bases 1,050-1,076) (SEQ ID NO: 1); antisense, 5'-TAAAGGTCTTCTTGGTGATGCC-3' (bases 1,511-1,535) (SEQ ID NO: 2). For NOS2, primers are as follows: 5' (sense), 5'-GCCTCGCTCTGGAAAGA-3' (bases 1,425-1,441) (SEQ ID NO: 3); antisense, 5'-TCCAT-GCAGACAACCTT-3' (bases 1,908-1,924) (SEQ ID NO: 4). Glyceraldehyde-3-phosphate dehydrogenase (GAPDH) MRNA is amplified from the same amount of RNA at the same time to correct for variation between different samples. The PCR products, separated on 1% agarose gels, are scanned and quantitated using Image-Quant software (Molecular Dynamics).

For Northern analysis of NOS1 and NOS3 MRNA levels in hearts of NOS2-/- and wild-type mice, total RNA is prepared from freshly excised hearts, subjected to electrophoresis on 1% paraformaldehyde-agarose gel, transferred to the GeneScreen Plus membrane (Dupont), and probed with random-primed mouse NOS1 and NOS3 cDNA probes. GAPDH cDNA probe is used to control for loading. Quantification is achieved using Image-Quant software.

Role of NOS2 The studies suggest that the NOS2 isoform is the primary NOS isoform responsible for FGF-2-induced preservation of myocardial function in this model. To further corroborate these results, the same studies are repeated in hearts from NOS2-/- mice using their NOS2+/+ littermates as controls. As in the case of previous studies, ischemia in both NOS2+/+ and NOS2-/- hearts is characterized by an abrupt fall in LV pressure, a gradual onset of ischemic contracture, and prolonged ventricular dysfunction throughout 20 min of reperfusion. rFGF-2 pretreatment prolonged T.sub.LVP10, reduces the onset of contracture, and improves LV recovery throughout reperfusion. However, in NOS2−/− hearts, rFGF-2 fails to provide any protective effects against global ischemia and stunning as measured by changes in LVP, dP/dt.sub.max, and dP/dt.sub.min after 20 min of reperfusion.

Release of NO and FGF-2 Effects on NOS Gene Expression To directly demonstrate the role of rFGF-2-induced NO release, the concentration of NO in coronary effluent before and after rFGF-2 administration is measured. NO concentration increases significantly after perfusion with rFGF-2 compared with measurements after perfusion with vehicle (236.+−.24 vs. 190.+−.25 nM/g, P<0.05) in wild-type hearts. In contrast, perfusion with rFGF-2 do not increase NO concentration in NOS2−/− hearts compared with NO values measured after perfusion with vehicle (170.+−.24 vs. 154.+−.46 nM/g, P=NS). To assess whether rFGF-2 increased NO production by stimulating NOS enzyme or increasing its gene expression, we carry out RT-PCR analysis of NOS2 and NOS3 mRNA levels before and after 40 min of exposure to rFGF-2. No differences in either NOS2 or NOS3 levels are detected.

The "knockout" of the NOS2 gene may affect expression of NOS1 or NOS3 genes in these mice. To evaluate this possibility, we perform Northern analysis of NOS1 and NOS3 gene expression in hearts from C57/BL6 NOS2+/+ and NOS2−/− mice. No significant changes in expression of either gene compared with that in control mice is detected.

Statistical Analysis Observations made before and after drug administration are compared using Student's two-tailed paired t-test. Observations made before and after the ischemia-reperfusion protocol within a group are compared using Student's two-tailed paired t-test. Between-group comparisons are made using analysis of variance. When an overall significance is observed, multiple comparisons are performed using the Bonferroni-modified t-test. A value of P<0.05 is considered significant. Data is expressed as means.+−.SE.

Baseline Conditions and Effects of Ischemia Baseline parameters of cardiac function including myocardial Ca.sub.i.sup.2+ are similar at baseline in all groups and are not affected by administration of L-NAME, L-NIL (not shown), or rFGF-2. Interruption of coronary flow leads to an abrupt fall in LV pressure in all hearts. This fall in LV pressure during early ischemia is significantly attenuated in hearts pretreated with rFGF-2 compared with control hearts. Pretreatment with rFGF-2 prolongs T.sub.LVP10 (124.+−.9 vs. 74.+−.5 s, rFGF-2 vs. control, P<0.05) and significantly delays the onset of contracture (893.+−.7 vs. 819.+−.36 s, rFGF-2 vs. control, P<0.01).

To explore the role of NO in mediation of this cardioprotective effect of FGF-2, L-NAME is used to inhibit all isoforms of NOS in the heart. Pretreatment with L-NAME completely blocks the cardioprotective effects of rFGF-2 during ischemia, significantly reducing T.sub.LVP10 (79.+−.2 vs. 124.+−.9 s, L-NAME+rFGF-2 vs. rFGF-2, P<0.05) and accelerating the onset of ischemic contracture (674.+−.24 vs. 893.+−.7 s, L-NAME+rFGF-2 vs. rFGF-2, P+0.05). However, perfusion with L-NAME alone (in the absence of rFGF-2) does not affect either T.sub.LVP10 [69.+−.3 vs. 74.+−.5 s, L-NAME vs. control, P+not significant (NS)] or the onset of ischemic contracture (820.+−.24 vs. 819.+−.36 s, L-NAME vs, control P+NS).

To further define the type of NOS enzyme involved in this FGF-2 response, a NOS2-selective inhibitor, L-NIL is used, Similarly to L-NAME, L-NIL fully inhibits the cardioprotective effects of rFGF-2, significantly reducing T.sub.LVP10 (62.+−.3 vs. 124.+−.9 s, L-NIL+rFGF-2 vs. rFGF-2, P<0.05) and accelerating the onset of Ischemic contracture (652.+−.16 vs. 893.+−.7 s, L-NIL+rFGF-2 vs. rFGF-2, P<0.05). Similarly to perfusion with L-NAME, perfusion with L-NIL alone, in the absence of rFGF-2, does not affect either T.sub.LVP10 (67.+−.6 vs. 74.+−.5 s, L-NIL vs. control, P+NS) or the onset of ischemic contracture (740.+−.39 vs. 819.+−.36 s, L-NIL vs. control, P+NS).

EXAMPLE 4

Efficacy of Intracoronary Versus Intravenous FGF-2 an a Porcine Model of Chronic Myocardial Ischemia A porcine ameroid model is chosen for preclinical testing of delivery strategies because of several unique aspects. First, the ameroid occluder results in consistent and gradual occlusion of the LCX, resulting in minimal myocardial necrosis, but reduced regional myocardial function, which is detectable with various noninvasive imaging modalities. Because an effect of estrogen on cardiac angiogenesis cannot be ruled out and synchronization of these studies with the menstrual cycle is logistically impossible, females are excluded from this study. In a similar model in dogs, daily intracoronary injections of FGF-2 also induce increased vascularity of ischemic myocardium. Although very encouraging, there is little data considering the efficacy of single intravascular administration of angiogenic growth factors.

MATERIALS AND METHODS Male Yorkshire pigs (n=57; Parsons, Hadley, Mass.) weighing 15 to 30 kg are used for this study. The chronic ischemia model consists of three phases as previously described [4, 7]. In brief, for ameroid surgery and catheterization at 3 and 6 weeks, the animals are anesthetized with Ketamine 20 mg/kg IM and pentothal 10 mg/kg IV, intubated, mechanically ventilated, and further anesthetized with 1.5% to 2.5% isoflurane in room air. Postoperatively, all animals receive antibiotics and analgesics for 48 hours. Animal care is performed according to the National Institutes of Health's Guidelines for the Care and Use of Laboratory Animals, and the protocol is approved by the Institutional Animal Care Committee.

A plastic ameroid (inner diameter, 2 to 2.5 mm; Research Instruments, Escondido, Calif.) is placed on the proximal left circumflex artery (LCX) or a major side branch, through a left lateral fourth intercostal thoracotomy. Three weeks (second phase, midstudy) later, right and left coronary catheterization is performed through a standard femoral cut-down after systemic anticoagulation with Heparin 100 U/kg. Intraarterial pressure and electrocardiogram are continuously recorded. Selective left and right angiography (General Electric, Waukesha, Wis.; contrast: Renografin; Squibb Diagnostics, Princeton, N.J.) confirms complete occlusion of the LCX and allows assessment of baseline flow and the presence of collaterals in the LCX territory, according to the Rentrop scoring system from 0 to 3: 0=none; 1=filling of side branches of the LCX; 2=partial filling of the LCX main artery via collateral channels; 3=complete filling of the LCX. Angiographic analysis is blinded to treatment. For regional blood flow measurements, colored microspheres are injected into the left atrium (see below). Directly after this, function, perfusion, and collateral sensitive magnetic resonance imaging (MRI) is performed on all animals to quantify baseline regional cardiac function and perfusion before start of the treatment.

Pigs are then randomly assigned to one of the following treatments: 1) vehicle control; 2) 2.mu.g/kg rFGF-2 IV; 3) 6 .mu.g/kg rFGF-2 IV; 4)2 .mu.g/kg rFGF-2 IC; 5) 6 .mu.g/kg rFGF-2 IC. Five minutes before FGF-2 administrations, heparin (70 U/kg, IV) is given. Bovine recombinant FGF-2 (rFGF-2; Chiron Corporation, Emeryville, Calif.) is dissolved and diluted in vehicle consisting of 10 mmol/L sodium citrate, 10 mmol/L thioglycerol, 135 mmol/L sodium chloride, 100 mmol/L EDTA, pH 5.0. The intracoronary FGF-2 is equally divided and infused into the right coronary artery (RCA) and the proximal LCX using a 3F Cordis infusion catheter. Intravenous infusions are given through an ear vein. In short proximal LCX stumps, FGF-2 is delivered into the proximal part of the LAD. The vehicle control group consists of animals that receive intravenous vehicle (n=4) or intracoronary vehicle (n=4). Three weeks after therapy (third phase, final study), repeat selective angiograms are made and two sets of colored microspheres are injected into the left atrium, one before (rest) and one after injection of Adenosine 1.25 mg/kg IV (stress). Function and perfusion MRI is also repeated in all animals. Finally, animals are euthanized and the hearts are excised.

Fifty-seven animals receive an ameroid constrictor and 13 animals die before initiation of treatment. Forty-four animals (control, n=10; FGF 2 .mu.g/kg IV, n=9; FGF 6 .mu.g/kg IV, n=9; FGF 2 .mu.g/kg IC, n=8; and FGF 6 .mu.g/kg IC, n=8) complete the entire study.

Regional blood flow For microspheres injection into the left atrium, a 7F JL4 catheter is retrogradely advanced across the aortic and mitral valve into the left atrium. The left atrial position of the catheter is confirmed by contrast injection and the presence of an atrial pressure waveform. At midstudy, and during the final study at rest and stress, 6.times.10.sup.6 microspheres (Dye Trac; Triton Technologies, San Diego, Calif.) are injected according to a standard protocol Reference blood samples were drawn simultaneously. At the end of the study (final study), a mid papillary, 1-cm-thick cross section of left ventricle is taken and divided into eight radial segments. The segment in the LCX territory is further subdivided in an endocardial and epicardial piece. Tissue samples and reference blood samples are digested and the microspheres retrieve according to the manufacturers protocol. The samples are analyzed with a spectrophotometer (SU 600; Beckman, Fullerton, Calif.). From the optical density (OD) measurements, the myocardial flow is calculated as blood flow: (tissue sample X; mL/min/g)=[withdrawal rate (mL/min)/weight (tissue sample X; g)].times.[OD (tissue sample X)/OD (reference blood sample)], using the Excel worksheet and macros provided by the manufacturer.

Hemodynamic parameters Intravenous infusion causes a mild but significant decrease in blood pressure of 12.3.+−.3.7 mm Hg (p=0.02) in the FGF 2 .mu.g/kg IV group and 9.6.+−.2.1 mm Hg (p=0.01) in the FGF 6 .mu.g/kg IV group. After intracoronary infusion, the drop in blood pressure is significant only at 2 .mu.g/kg with 10.0.+−.2.2 mm Hg (p=0.04) and not at 6 .mu.g/kg (6.1.+−.4.9 mm Hg, p=0.25). In all groups, heart rate decreases mildly, ranging from 2 to 15 bpm, but is significant only in the FGF 2 g/kg IV with 9.+−.4 bpm (p=0.05) and 6 .mu.g/kg IC group with 18.+−.6 bpm (p=0.03).

Coronary angiography Seven follow-up angiograms, two in the control group, two in the FGF 2 .mu.g/kg IV, one in the FGF 6 .mu.g/kg IV, and two in the FGF 2 .mu.g/kg IC group, are not available for analysis. Collateral index improves significantly in the 6 .mu.g/kg IV group and in both 2 and 6 .mu.g/kg IC groups, whereas baseline collateral index is similar (p=0.1 19, Kruskal Wallis). For all groups pooled, collateral index results from left-to-left collaterals (either LAD to LCX or LCX to LCX, n=37; p<0.001, McNemar test) and not from right-to-left (p=1.0), suggesting a localized effect of intravascular drug delivery. However, changes are not significant in any subgroup.

Coronary blood flow. Baseline regional blood flow in the ischemic (LCX) and normal (LAD) territories is measured at rest and post treatment (final study) at rest and stress (adenosine). Absolute ischemic flow (mL/min/g tissue) and the LCX/LAD flow ratio are determined. LAD flow at baseline, rest, and stress at the final study are similar in the five groups (ANOVA, p=0.363, p=0.418, and p=0.331, respectively). Rest LAD flow does not change significantly over time (ANOVA, p=0.266). In addition, LCX coronary blood flow at baseline (before FGF2 infusion) is similar in all five groups (ANOVA, p=0.361). At the final study at rest, absolute LCX flow and the LCX/LAD ratio do not change significantly. However, LCX flow at stress is significantly higher in the FGF 6 .mu.g/kg IC group than in controls (ANOVA, p=0.039).

Myocardial MRI analysis. Arterial pulse-gated MRI is performed on anesthetized (1% to 2% isoflurane) and ventilated animals, in the body coil of a 1.5-Tesla whole-body (Siemens, Munich Germany) Vision prototype. Baseline anatomic images are obtained by a turboFLASH technique to identify coordinates for apical four-chamber, two-chamber, and short-axis views. For function studies, 24 sequential image frames are collected over 12 heartbeats during breathhold using shared-center turboFLASH in each of the three standard views. After detection of the optimal inversion time (TI; typically 200 to 300 ms), a series of 32 diastolic images are acquired in the double-oblique four-chamber view during breath-hold, while injecting 0.05 mmol/kg gadodiamide (T1-reducing contrast agent). The series of images is viewed as a movie, to locate the zone with impaired contrast arrival. The short axis at the center of that zone (target zone) is prescribed graphically. All measurements are performed by two independent investigators blinded to treatment. Custom-designed software is used to define myocardial borders and measure wall thickness. End-systolic and end-diastolic left ventricular volumes are computed from biplane measurement (apical four-chamber and two-chamber views) as previously validated, and used to calculate left ventricular ejection fraction. Target wall motion (radial shortening) and target wall thickening are expressed as percentage of the radial length or wall thickness at the end of diastole. Both parameters are also measured at the septum, yielding normal target wall motion and target wall thickening. The area of delayed contrast arrival is defined as myocardium demonstrating distinctly slowed time (.gtoreq.1 cardiac cycle) to half-maximal signal intensity, using a two-dimensional map of contrast intensity versus time.

MRI: left ventricular function Infarct size visualized as myocardium without MRI contrast uptake is measured to avoid confounding of regional function and perfusion measurements. Infarct size is similar among the five groups at either baseline (3 weeks) or final study (ANOVA, p=0.594 and p=0.303, respectively). Infarct size, 3.0%.+−.4.9% left ventricular area (mean.+−.SD), is within the range reported for this model.

Left ventricular ejection fraction (EF) at baseline is similar for all treatment groups (ANOVA, p=0.120). Using each animal as its own control, EF improves significantly in controls (p=0.018), in the FGF 2 .mu.g/kg IV (p=0.046), the FGF 6 .mu.g/kg IV (p=0.001), and the FGF 6 .mu.g/kg IC groups (p=0.001). The improvement in EF after treatment is significantly higher in the FGF 6.mu.g/kg IC (p<0.01) group compared with controls. The improvement in indexed target wall motion (target wall motion/normal wall motion) is significant only in the FGF 6 .mu.g/kg IV (p=0.019) and the FGF 6 .mu.g/kg IC groups (p=0.004), whereas indexed target wall thickening improves in the FGF 6 .mu.g/kg IC group (ANOVA, p=0.007 compared with improved target wall thickening in controls, p=0.001).

MRI: perfusion. At baseline, no differences in areas of delayed arrival (ANOVA,p=0.140) or collateral extent (p=0.103) is found between the groups. The size of the zone of delayed arrival decreases in the FGF 6 .mu.g/kg IC (p<0.001), which is significantly different from the change in controls (ANOVA,p<0.001).

Toxicologic assessment of FGF-2 administration. Before treatment and at necropsy, blood samples for hematology, coagulation, and serum chemistry are obtained from at least three fasted animals per group. Hematology parameters include hemoglobin, mean corpuscular hemoglobin concentration, hematocrit, erythrocyte count, total leukocyte count, differential, platelet count, mean corpuscular hemoglobin, and mean corpuscular volume. Serum chemistry include aspartate aminotransferase, alanine aminotransferase, gamma glutyltransferase, alkaline phosphatase, lactate dehydrogenase, total bilirubin, total cholesterol, triglycerides, blood urea nitrogen, creatinine, creatine phosphokinase, albumin, globulin, total protein, electrolytes (Na, K, and Cl), calcium, phosphorus, and glucose.

In addition, for four randomly selected animals in each treatment (not vehicle) group, tissue samples are taken from major organs and processed for histology. Histopathological findings are graded on a scale of 1 to 4 (minimal<mild<moderate<marked), by a veterinary pathologist blinded to treatment.

There is no macroscopic or microscopic lesions related to intravenous or intracoronary administration of FGF-2. Furthermore, no changes in hematological or biochemical parameters are observed in any of the treatment groups.

In this study, in which the efficacy of intravenous and intracoronary delivery of 2 or 6 .mu.g/kg FGF-2 is compared, blood supply to the myocardium, as assessed by the colored microsphere method, is improved by the high-dose (6 .mu.g/kg) intracoronary FGF-2. Although this effect is only significant at stress, the same trend is seen for regional blood flow at rest. Both intravenous FGF-2 doses as well as the 2-.mu.g/kg dose are ineffective. This change in regional blood flow is confirmed by perfusion and collateral-sensitive MRI, and had functional significance because it is accompanied by an increase in EF and improvement in target wall motion and target wall thickening in the high-dose intracoronary group, The effect on EF is added to the natural tendency to grow collaterals and improve perfusion and function of ischemic myocardium.

The current study presents evidence that a single intracoronary injection of 120 to 150 .mu.g FGF-2 improves regional blood flow as well as regional and global cardiac function. The ineffectiveness of intravenous FGF-2 might result from less favorable pharmacokinetics. Several studies have reported a 3- to 10-fold lower recovery of radiolabeled FGF-2 from the myocardium after intravenous administration than after intracoronary injection, which in turn has a lower recovery and shorter redistribution times than intrapericardially delivered FGF-2. FGF-2 might be retained in the myocardium by a high-capacity, low-affinity sink provided by heparin sulfates in the matrix and on the surface of endothelial cells, which are upregulated by ischemia. In addition, expression of FGF-R1 receptors, which are the primary transducers of FGF-2 signaling, is also upregulated by ischemia.

In this animal study, in accordance with the phase I clinical trial, intravenous FGF-2 and 2 .mu.g/kg intracoronary FGF-2 have no major hemodynamic, hematotogic, or biochemical side effects.

Clinical implications If a single intracoronary infusion of FGF-2 proves to be effective in patients with chronically ischemic myocardium, this strategy will greatly increase the number of patients that might benefit from adjunctive growth factor therapy, especially in view of the minimal side effects. Each patient undergoing percutaneous revascularization is a candidate for angiogenic therapy because most interventions are local and aimed at the most severe stenoses in epicardial arteries. The additional benefit of myocardial salvage during reperfusion injury by FGF-2 further emphasizes the potential value of this adjunct pharmacotherapy.

It is concluded that a single 6-.mu.g/kg intracoronary FGF-2 delivery results in-significant improvement in collateralization and regional and global function of chronically ischemic myocardium. A single intravenous infusion of FGF-2 is ineffective in the doses tested. A phase 11 clinical trial of patients with coronary artery disease designed to evaluate this intracoronary therapeutic strategy is currently underway.

EXAMPLE 5

Local Perivascular Delivery of FGF-2

In this trial, patients with a viable and ischemic myocardial area that could not be revascularized were randomized to receive heparin-alginate pellets containing 10 or 100 .mu.g of bFGF or placebo that were placed on the epicardial surface during CABG.

Patient Selection. The study population consisted of patients undergoing CABG at Beth Israel Deaconess Medical Center and Albert Einstein College of Medicine in Boston, Mass. The inclusion criteria included an area of myocardium supplied by a major coronary artery with advanced disease not amenable to bypass grafting or percutaneous intervention, inducible ischemia, and the ability to understand and sign the informed consent and to comply with planned follow-up. Patients with the following criteria were excluded from consideration for the study: absence of inducible ischemia or myocardial viability of the target area, hypertrophic or restrictive cardiomyopathy, left ventricular ejection fraction<20%, significant valvular heart disease, renal dysfunction (serum creatinine>2.5 mg/dL), history of malignancy within the previous 5 years, or unexplained hematological or chemical abnormalities before CABG.

The design and performance of the study were approved by the Food and Drug Administration under an investigatorsponsored investigational new drug (BB-IND 5725). The study was approved by the Committee for Clinical Investigation at both institutions. The first patient was enrolled in September 1996 and the last patient in May 1998.

Patient Population and Enrollment Procedure. Seventy-eight patients scheduled for CABG were screened for enrollment into the study on the basis of an angiogram that showed a major epicardial coronary artery (posterior descending artery, significant diagonal, obtuse marginal, or ramus intermedius branch, or significant posterolateral branch) that was considered by an interventional cardiologist and a cardiothoracic surgeon not involved in the study unlikely to be graftable on the basis of its angiographic appearance (diffusely diseased or heavily calcified). Patients were approached for enrollment in the study, and screening tests were performed to ensure that all eligibility criteria were met, including demonstrable ischemia in the target myocardial area. Forty-six patients who met all eligibility criteria and agreed to participate in the study underwent CABG, during which a noninvestigator cardiac surgeon determined whether the target area was indeed ungraftable. Bypass surgery of the target vessel was performed in 22 cases, and those patients were excluded from additional study. The remaining 24 patients (19 patients at Beth Israel Deaconess Medical Center and 5 at Montefiore Medical Center, Bronx, N.Y.) who had a coronary artery that could not receive a graft at the time of surgery were randomized to receive 10 heparin-alginate pellets containing placebo or 1 of 2 doses of bFGF (10 or 100 .mu.g). There was no significant difference between the study groups in any of the clinical parameters, including the extent of coronary disease or presence of any risk factor, except that patients in both 10- and 100-.mu.g bFGF treatment groups were somewhat older than controls, and there were more women in the 10-.mu.g bFGF group. The baseline resting ejection fraction was 50.3.+-.13.8%, and 5 of the 24 patients had an ejection fraction<30%.

Preparation of bFGF-Containing Heparin-Alginate Pellets. Calcium alginate pellets provide a stable platform for bFGF because of enhanced retention of activity and storage time and thus were used as devices for controlled bFGF release in vivo. Heparin-sepharose beads (Pharmacia LKB) were sterilized under ultraviolet light for 30 minutes and then mixed with filter-sterilized sodium alginate. The mixed slurry was dropped through a needle into a beaker containing a hardened solution of CaCl.sub.2 (1.5% wt/vol). Beads formed instantaneously. Uniformly cross-linked capsule envelopes were obtained by incubating the capsules in the CaCl.sub.2 solution for 5 minutes under gentle mixing and then for 10 minutes without mixing. The beads were washed with sterile water and stored in 0.9% NaCl-1 mmol/L CaCl.sub.2 at 4.degree. C. bFGF loading was performed by incubating 10 capsules in 0.9% NaCl-1 mmol/L CaCl.sub.2 –0.05% gelatin with 12.5 p (for 10-.mu.g dose) or 125 mu. (for 100-.mu.g dose) of bFGF (GMP grade human recombinant bFGF provided by Scios, Inc) for 16 hours under gentle agitation at 4.degree. C. Previous studies have shown that under these conditions, 80% of bFGF in solution is absorbed into heparin-alginate pellets. The end product was sterilized under ultraviolet light for 30 minutes. With each preparation, several beads were cultured to ensure sterility. Blank or bFGF-loaded pellets were identical in appearance, which ensured that the surgeons and investigators were blinded with regard to which pellet was being used.

bFGF Heparin-Alginate Delivery After completion of coronary bypasses to all areas of the heart that could be revascularized and failure to graft the target vessel (which on occasions involved probing of the target vessel), multiple linear incisions were made in the epicardial fat surrounding the target vessel. Heparin-alginate pellets (containing bFGF or placebo) were inserted into the epicardial fat overlying the artery and secured in place by a 6.0 prolene suture to close the subepicardial incision. A total of 10 pellets were used in each patient (2 to 3 pellets were placed in each incision). The left internal mammary artery (LIMA) was placed on the left anterior descending artery (LAD), and proximal vein-to-aorta anastomoses were constructed. Ventilation was reestablished, and cardiopulmonary bypass was terminated. Routine closure was then performed.

Short-Term Results. The extent of CABG surgery was the same in all treatment groups; there were no significant differences with regard to the number of grafts, duration of surgery (average 3.0.+-.0.9 hours), or cross-clamp time (average 56.+-.13 minutes). The target vessel was the right coronary artery (RCA) in 15 patients, left circumflex artery in 7, and diagonal branch of the LAD in 2.

One patient in the control group died 24 hours after surgery secondary to an autopsy-documented occlusion of one of the saphenous vein grafts, with a large myocardial infarction in that territory. A second death occurred in a patient in the 100-.mu.g bFGF group who could not be weaned off cardiopulmonary bypass (preoperative ejection fraction of 20%); an autopsy revealed patent grafts with extensive myocardial scarring and a thin rim of epicardial viable myocardium. Two other patients (both in the control group) required intra-aortic balloon pump support after surgery (in 1 patient, the intra-aortic balloon pump was inserted before surgery). Two patients (1 in the control group and 1 in the 10-.mu.g bFGF group) had a Q-wave myocardial infarction in the target myocardial distribution, and 1 patient in the 10-.mu.g bFGF group had a Q-wave myocardial infarction in a nontarget myocardial distribution.

Placement of bFGF-containing heparin-alginate microspheres had no significant short-term effects on blood pressure or heart rate; the mean arterial pressure was 84.8.+-.10.6 mm Hg before bypass, 89.+-.12 mm Hg on day 1, 93.+-.7 mm Hg on day 3, and 83.4.+-.11.1 mm Hg on day 5 and was not different among the treatment groups. Pharmacokinetic evaluation did not reveal any significant increase in serum bFGF levels above baseline in any of the groups (average bFGF levels in 15 patients: 17.4.+-.3.3, 15.90.+-.1.4, 15.9.+-.1.8, and 16.+-.1.8 .mu.g/mL at baseline and postoperative days 1, 3, and 5, respectively), and there were no significant differences in bFGF levels between the different treatment groups. The average postoperative hospital stay was 5.30.+-.1.3 days (range 4 to 8 days). There were no acute effects on serum chemistries, hematologic and coagulation profiles, liver function tests, or urinalysis. Two patients developed superficial wound infections along the chest incision that necessitated surgical debridement, and another patient with diabetes mellitus had delayed healing of the saphenous vein graft harvest site. Microbiological evaluation of the beads showed no aerobic or anaerobic growth in samples from 28 of the 46 preparations.

In-Hospital Follow-Up. The postoperative course was evaluated, including-hemodynamic parameters, duration of ventilatory support, postoperative ECGs, postoperative cardiac isoenzymes, duration of hospitalization, and any evidence of infection. Serum bFGF levels were measured (ELISA, R&D Systems) before implantation and on the first, third, and fifth postoperative days. Complete blood count, coagulation parameters, serum chemistries, and urinalysis were performed before treatment and at days 3 and 5 after treatment In the first 10 patients, stress nuclear perfusion imaging and MRI (at the Beth Israel Deaconess Medical Center) were performed before CABG; however, owing to the confounding effect of CABG (realized after an interim analysis of the first 10 patients by the Data Safety and Monitoring Committee), the remaining patients underwent stress nuclear perfusion scans (rest-thallium/dipyridamole sestamibi) and MRI after CABG (before discharge). The surgeon, other investigators, and patients were blinded to treatment assignment.

Long-Term Follow-Up. All patients were contacted by the investigators at 6 weeks; 2, 3, 4, and 6 months; 1 year; and then yearly thereafter to assess clinical events (death, myocardial infarction, recurrent angina, or any repeat revascularization). Complete blood count, coagulation parameters, serum chemistries, urinalysis, and serum bFGF level measurements were repeated at 3 months. Patients underwent stress nuclear scans at 3 months (dual-isotope studies with rest thallium and stress [pharmacological stress with dipyridamole sestamibi]). In addition, patients at the Beth Israel Deaconess Medical Center underwent repeat MRI 3 months after CABG. Clinical follow-up of .gtoreq.6 months was available for all patients, with a mean follow-up of 16.0.+-.6.8 months.

Clinical Follow-Up. Clinical follow-up was available in the 22 surviving patients (7 from the placebo group, 8 from the 10 .mu.g-bFGF group, and 7 from the 100 .mu.g-bFGF group) and averaged 16.0.+-.6.8 months. At last follow-up, all patients were angina-free except for 3 patients in the placebo group (Canadian Cardiovascular Society [CCS] class II in 1 and class III in 2 patients) and 1 patient in the 10-.mu.g bFGF group (CCS class II). Two of the 3 placebo patients with angina underwent successful percutaneous revascularization (1 involved the target vessel and the second involved a vein graft stenosis). After hospital discharge, none of the patients died or sustained a myocardial infarction. There were no delayed wound infections, no clinical evidence of pericarditis, and no other adverse events. Laboratory evaluation at 90 days (available in 21 patients) did not show any adverse effect on complete blood count, coagulation parameters, serum chemistries, or urinalysis.

Imaging Studies. Rest thallium/dipyridamole sestamibi studies were performed according to the ADAC protocol. We compared baseline and 90-day nuclear scans using the size of the stress perfusion defect, as determined by pixel analysis. MRI was performed in the body coil of a 1.5-T whole-body Siemens Vision system. Baseline anatomic images were obtained by a turboFLASH (turbo Fast Low-Angle SHot) technique to identify coordinates for apical 4-chamber, 2-chamber, and short-axis views. Functional imaging was performed during breathhold by use of shared-center turboFLASH in each of the 3 mutually perpendicular standard views, producing 24 sequential image frames each, collected over 12 heartbeats to measure regional wall motion. MR perfusion imaging was performed as follows: a series of 4 inversion recovery images (1 every second heartbeat) was obtained as inversion time (TI) and adjusted to minimize the signal intensity from myocardium in the fourth frame. With the best TI determined by these scout images, a series of concurrent parallel images were acquired in diastole during breathhold, 1 every other heartbeat, at baseline and again with contrast injection (0.05 mmol/kg gadodiamide). In addition, complete blood count, coagulation parameters, serum chemistries, urinalysis, and serum bFGF level measurements were repeated at 3 months.

Nuclear Perfusion Imaging. Twenty of the surviving 22 patients underwent stress nuclear perfusion imaging 90 days after CABG. In the first 10 patients, baseline studies were performed before CABG. It became clear as the study progressed, however, that this was not a true baseline because of the confounding effect of CABG. Therefore, in the remaining 12 patients, rest-thallium/dipyridamole sestamibi nuclear testing was performed after CABG and before hospital discharge. The baseline stress target area defect size was 20.6.+-.5.2% of the left ventricle and was similar in all 3 treatment groups (22.3.+-.5.4% in controls, 19.2.+-.5.0% for the 10-.mu.g bFGF group, and 20.4.+-.5.7% for the 100-.mu.g bFGF group, ANOVA P=0.56). At the time of follow-up nuclear scans, when paired t tests were used, there was a trend toward worsening (increase in the defect size) in the placebo group (20.7.+-.3.7% at baseline to 23.8.+-.5.7% at follow-up, P=0.06). Studies in the 10-.mu.g bFGF group showed no change in defect size(19.2.+-.5.0% to 16.9.+-.8.1%, P=0.39), whereas defect size in the 100-.mu.g bFGF group was significantly improved compared with baseline (19.2.+-.5.0% to 9.1.+-.5.9%, P=0.01). The change in defect size was significantly different among the 3 groups (ANOVA P=0.005). Semiquantitative analysis of stress images demonstrated worsening of the defect in 3 of 6 patients and no change in 3 of 6 patients in the control group. Of 8 patients in the 10-.mu.g bFGF group, the target nuclear defect size worsened in 2 patients, remained unchanged in 2, and improved in 4. Finally, of the 6 patients in the 100-.mu.g bFGF group who underwent follow-up nuclear testing, there was improvement in 5 patients and no change in 1 patient.

Magnetic Resonance Imaging. Functional and perfusion MRI were performed in 8 patients at the Beth Israel Deaconess Medical Center at baseline and at 90-day follow-up (4 controls and 4 bFGF-treated patients [1 patient in the 10-.mu.g bFGF group and 3 in the 100-.mu.g bFGF group]). Baseline resting target wall motion (radial wall motion) was 21.7.+-.6.7% in the placebo group and 27.3.+-.17.0% in patients treated with 100 .mu.g of bFGF (compared with 35.7.+-.10.9% for normal revascularized wall). No changes in resting target wall motion were seen at follow-up (23.7.+-.9.3% in placebo and 32.3.+-.12.4% in 100-.mu.g bFGF-treated subjects). The extent of the resting delayed contrast arrival zone, which reflects underperfused myocardium, for placebo and bFGF-treated patients was 10.7.+-.3.9% and 15.7.+-.2.3% at baseline and decreased to 7.8.+-.6.9% (P=0.37) and 3.7.+-.6.3% (P=0.06) at follow-up, respectively, with a trend toward improvement in the 100-.mu.g bFGF group.

Because of the protracted course of new collateral development, the potential for hemodynamic disturbances associated with bolus intravascular delivery, and the possibility for toxicity from elevated circulating levels of angiogenic growth factors, a local sustained bFGF delivery strategy using heparin-alginate microcapsules was used. This delivery system allows prolonged (4 to 6 weeks) sustained release (first-order kinetics). In animal studies, there was a dose-dependent effect of bFGF that was not associated with detectable serum levels, hemodynamic effects, or locator systemic toxicity.

Of the 46 patients judged to have a major coronary artery that could not be grafted on the basis of angiographic appearance, 22 patients were actually successfully grafted at the time of CABG. Thus, preoperative assessment of arterial suitability for bypass proved to be inaccurate in almost 50% of cases. In accordance with prior observations, the major epicardial artery most likely to be unsuitable for grafting was the RCA. In no case was the LAD considered ungraftable. This paucity of LAD cases is probably a reflection of the reluctance to refer those patients in whom the LAD may not be bypassed for surgical intervention.

The combination CABG/bFGF therapy was not associated with an excess rate of complications. Two operative deaths in this study most likely reflect the higher operative risk in patients with advanced coronary disease and left ventricular dysfunction who have incomplete revascularization. The absence of hemodynamic abnormalities associated with heparin-alginate bFGF delivery is consistent with the undetectable serum levels of bFGF at any time after growth factor administration. In addition, the lack of short- or intermediate-term adverse effects on serum chemistries, hematologic profile, liver function tests, or urinalysis also suggests that this mode of delivery is not associated with systemic toxicity. These observations therefore emphasize the safety of heparin-alginate bFGF delivery at the time of CABG.

This randomized, double-blind, placebo-controlled study of bFGF in patients undergoing CABG demonstrates the safety and feasibility of this mode of therapy in patients with viable and isohemic but unrevascularizable myocardium. These results warrant a larger multicenter trial to assess the clinical benefit of this combination approach to myocardial revascularization, which is currently under way.

EXAMPLE 6

Reduction in Myocardial Infarct Size Following Intracoronary Administration of FGF-2

The extent of myocardial injury and necrosis resulting from an ischemic insult is determined by the duration of interruption to antegrade flow, the size of the compromised territory, and the extent of collateral circulation to the region. In view of the beneficial effects on myocardial viability and contractile function demonstrated in collateralized patients with occlusive coronary artery disease, these findings provide a rationale for investigation of new strategies that use growth factors such as bFGF to pharmacologically enhance collateral growth and to blunt the effects of impaired antegrade myocardial perfusion.

Coronary Occlusion and Reperfusion. Twenty-two mongrel dogs of either sex (weight, 17 to 23 kg) are randomly assigned to treatment with bFGF or vehicle. After the animals receive anesthesia with sodium pentobarbital (25 mg/kg IV), intubation, and ventilation with room air, the right carotid artery is exposed, ligated distally, and cannulated. Aortic blood pressure, heart rate, and ECG are monitored continuously throughout the procedure. After baseline left ventriculography is accomplished via a 6F pigtail catheter, selective left coronary angiography is performed via an 8F angioplasty guiding catheter. Because of the potential interaction between heparin and bFGF, intraprocedural anticoagulation is achieved with the use of Hirulog, a synthetic direct thrombin inhibitor; after an intravenous loading dose of 2.5 mg/kg, intravenous infusion is commenced at 5 mg.multidot.kg.sup.-1 .multidot.h.sup.-1 and the rate adjusted to maintain the activated clotting time at >300 seconds.

An angioplasty balloon catheter (balloon:artery ratio 1.0) is then inflated at 2 atm in the middle part of the LAD distal to the first diagonal branch, and occlusion is confirmed angiographically. After 4 hours' occlusion, the balloon catheter is deflated and removed, and LAD patency is confirmed angiographically. Ten micrograms of human recombinant bFGF (in 20 mmol/L sodium citrate, 1 mmol/L EDTA, and 9% sucrose, pH 5; Scios Nova Inc) in 10 mL normal saline or vehicle (10 mL normal saline) is administered directly into the left main coronary artery via the guiding catheter 10 minutes after occlusion and again just before reperfusion. After reperfusion, left ventriculography is repeated. All surgical procedures are performed with the use of a sterile technique. Seven days after the first procedure, dogs are anesthetized, intubated, and ventilated in the same manner as before. Patency is confirmed angiographically, left ventriculography is repeated, and euthanasia is performed with a lethal dose of pentobarbital.

Figure 4:
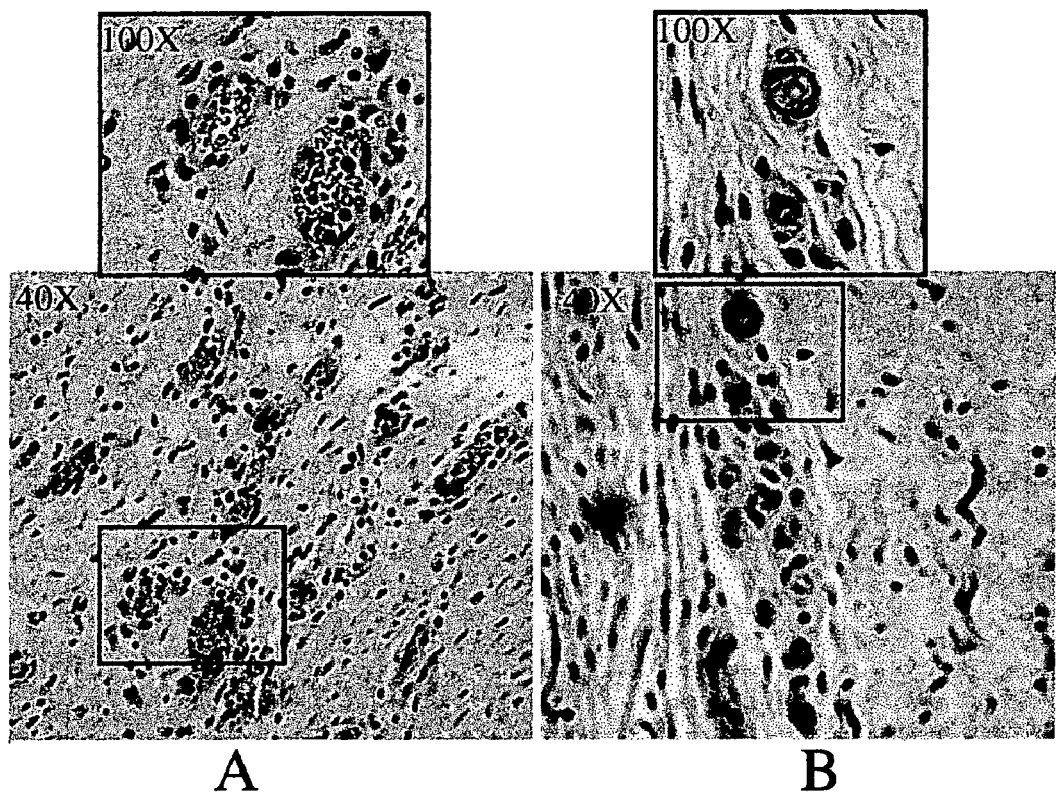
FIG. 4 is an illustration of histopathological sections from the LCX distribution demonstrating an increased number of capillaries in all treatment groups.

Occlusion-Reperfusion Study. Blood pressure and heart rate are similar in both groups throughout the experiment. Heart rate is increased during reperfusion in vehicle- and in bFGF-treated dogs (both P=0.043 versus baseline) because of nonsustained ventricular tachycardia and frequent ventricular ectopic activity. No systemic hemodynamic changes are noted after bFGF was administered. The areas at risk are similar in both groups (41.+−.8 cm.sup.2 versus 40.+−.6 cm.sup.2, vehicle versus bFGF). In the bFGF-treated group, infarct size expressed as a percentage of the area at risk was 13.7.+−.2.1%, which is significantly less than in dogs receiving vehicle (28.4.+−.3.4%; P=0.002; FIG. 3*). At baseline, left ventricular ejection fractions are similar in both groups (bFGF versus vehicle, 42.6.+−.1.9% versus 44.8.+−.3.5%). After reperfusion (bFGF versus vehicle, 33.1.+−.5.4% versus 40.3.+−.3.2%) and again at 1 week after infarction (bFGF versus vehicle, 33.6.+−.3.6% versus 38.8.+−.3.5%), ejection fractions show no significant difference between groups (FIG. 4*).

Microscopic examination of sections demonstrates concordance between triphenyltetrazolium chloride infarct delineation and histological features of myocardial necrosis. Although bFGF treatment is associated with significant myocardial salvage, there is no difference in the number of endothelial cells per high-power field within the infarcted region (bFGF versus vehicle, 241.+−.16 versus 221.+−.18 cells/hpf; P=0.8) or in the number of endothelial cells in the border zones (bFGF versus vehicle, 247.+−.18 versus 245.+−.15 cells/hpf; P=0.63). Because of the potential for spurious PCNA counts in areas of leukocyte infiltration, PCNA counts are obtained from border zones only; these counts are similar in both groups (bFGF versus vehicle, 10.1.+−.2.3 versus 7.3.+−.2.3 cells/hpf; P=0.4).

Measurement of Activated Clotting Time. Activated clotting time is measured with the use of the Hemochron 801 timer (International Technidyne Corp). After 2 mL of whole blood is collected into a Hemochron tube containing 12 mg of Johns-Manville diatomaceous earth, the time taken to complete coagulation at 37.degree. C. is measured.

Delivery and Biological Activity of bFGF. To ensure delivery of bFGF after passage through the manifold and angioplasty guiding catheter, radiolabeled bFGF is passed through new and used systems. To simulate the conditions of an in vivo experiment, 20 .mu.g of cold bFGF is mixed with 25 .mu.Ci of radiolabeled bFGF in 20 mL of normal saline solution. A second batch of 20.mu.g of cold bFGF is mixed with 25 .mu.Ci of radiolabeled bFGF in 20 mL of normal saline solution containing 1 mg/mL of dog albumin (Sigma Chemical Co). The number of counts per minute from both solutions is quantified in a scintillation counter. Ten-milliliter aliquots of the radiolabeled solutions are then delivered through used and new guiding catheters and manifolds and flushed with an additional 10 mL of normal saline. The number of counts per minute in the solutions collected after passage through the catheter system is measured. The difference in counts per minute between the incoming and outgoing solution is used as an index of bFGF loss within the delivery system. Under the conditions described above, there is minimal loss of activity in the delivery system. The bFGF used in the experiments is compared in a mitogen assay with human recombinant bFGF from a commercial source (Boehringer Mannheim) that has proven activity in previous assays. The potency of both lots of bFGF is similar, as assessed by .sup.3H-thymidine uptake after stimulation of cultured human fibroblasts (data not shown).

Determination of Infarct Size. After euthanasia and rapid excision of the heart, the LAD and circumflex arteries are cannulated individually. Simultaneously, at a pressure of 100 mm Hg, the circumflex vessel is perfused with Evans blue dye and the LAD with triphenyltetrazolium chloride for 10 minutes. Hearts are then fixed by perfusion with Histo-Choice (Ameresco) for 4 hours, after which the left ventricle is cut into 1-cm-thick slices perpendicular to its long axis, and the slices are weighed. With this technique, areas of viable tissue in the LAD distribution are stained red, necrotic areas remain white, and the circumflex territory is stained blue. For each slice, the area at risk, the area of infarction, and the circumflex territory are determined by computer-assisted planimetry, as previously described.

Histology and Immunohistochemistry. Multiple tissue samples are taken from areas of infarction and areas at risk of infarction for histological examination to seek evidence of neovascularization. Given the assumptions that (1) neovascularization of ischemic regions would proceed from the circumflex and nonoccluded LAD distributions and (2) the tissue stimulus for neovascularization would be intense in tissue adjacent to the infarct zone, "border-zone" samples are taken from the area at risk midway between the edges of the macroscopically infarcted myocardium and the junction of the LAD and circumflex territories. Staining with hematoxylin and eosin is used to confirm the presence of tissue necrosis in the infarct zones. Immunohistochemical staining of tissue samples is performed with factor VIII-related antigen to detect endothelial cells and PCNA to detect proliferating cells.

After being embedded in paraffin, 5-.mu.m sections are cut and collected onto glass slides coated with 1% polychloroprene in xylene. After being dried for 60 minutes at 60.degree. C., paraffin is removed in three changes of xylene. The tissue is then rehydrated through graded alcohols before being rinsed in PBS. Immunohistochemical staining is performed in a Jung Histostainer (Leica). A 0.6% hydrogen peroxide solution in PBS is then applied for 5 minutes to remove any endogenous peroxidase. For the PCNA sections, a blocking solution of 1:10 (vol/vol) normal rabbit serum (Dako Corp) is added for 10 minutes before application of a 1-in-50 dilution of murine monoclonal antibodies directed against PCNA (PC10 Clone, Dako Corp). For the factor VIII-related antigen stain, a blocking solution of 1:10 (vol/vol) normal swine serum (Dako Corp) is added for 10 minutes before application of a 1:300 dilution of rabbit polyclonal antibodies directed against factor VIII-related antigen (Dako Corp). The dilutions of the primary antibodies are prepared with the use of 1% BSA in PBS and are incubated with the tissue sample at 30.degree. C. for 60 minutes. A 1:200 dilution of biotinylated rabbit anti-mouse polyclonal antibody (Dako Corp) is then added for 30 minutes to the PCNA sections, and 1:200 biotinylated swine anti-rabbit polyclonal antibody (Dako Corp) is added to the factor VIII-stained sections for 30 minutes. These antibodies are labeled with an Elite streptavidin-biotin-peroxidase complex (Vector Laboratories) applied for 30 minutes. The final stage involves the addition of 3,3'-diaminobenzidine (Vector Laboratories) as a chromogen. Between steps, the sections are rinsed for 2 minutes in PBS. Slides are then rinsed in distilled water, dehydrated, cleared in xylene, and mounted in Permount (Fisher Scientific). In each staining preparation, sections treated with 1% BSA in PBS instead of with the primary antibody are included as negative controls, and sections of human tonsil are used as positive controls.

Cell Counts. Photographs of immunohistochemically stained tissue sections are taken without knowledge of treatment assignment. After low-power examination, five to seven representative fields (0.5.times.0.34 mm) are photographed from each section at a magnification of 200.times. Whenever possible, consecutive adjacent fields are photographed. In sections from the infarct zone, fields with relative preservation of tissue architecture are selected, obviating spurious increases in vessel density due to preservation of vascular structures in areas of parenchymal loss and stromal collapse. Cells that stained positive for PCNA and factor VIII (regardless of the presence of a vascular lumen) are counted by two independent observers blinded to treatment assignment (interobserver correlation coefficient, r=0.69; P<0.0001). Immunostaining for factor VIII and PCNA represent the techniques currently used as diagnostic tools for measurement of tumor angiogenesis.

Left Ventricular Ejection Fraction. Left ventricular ejection fractions are determined from single-plane left ventriculograms measured by a trained technician who is blinded to treatment assignment. Ejection fractions are calculated by use of the length-area method with a computer analysis package (Angiographic Ventricular Dynamics 5.1, Siemens).

Acute Hemodynanlic Studies In five additional dogs of either sex (weight, 19 to 22 kg), we compare the effects of intracoronary bFGF on coronary hemodynamic parameters with those of temporary coronary occlusion and intracoronary NTG. The studies are performed with the use of a standard open-chest model in which the LAD is isolated and instrumented with a Doppler flow probe to measure blood flow (Crystal Biotech). A 2F catheter is advanced retrogradely via a small proximal branch of the LAD into the left main vessel for administration of drugs. Blood flow responses after 10- and 20-second periods of LAD occlusion and after incremental doses of intracoronary NTG (1, 10, and 100 .mu.g) are recorded to confirm the presence of coronary vascular reactivity. Incremental doses of intracoronary bFGF (1, 10, and 100 .mu.g) are then given, and coronary flow responses are measured. bFGF (buffered as described above) and NTG solutions are prepared in 1 mL of normal saline just before administration and are given as boluses over 20 seconds. Blood pressure, heart rate, and ECG are monitored continuously throughout the procedure. Coronary vascular resistance (CVR) is calculated according to the formula:

$$CVR(mmHg\cdot mL^{-1}) = \text{mean aortic pressure (mm Hg)} \times 1/(\text{coronary flow (mL/min)})$$

The results of the occlusion-reperfusion study demonstrate a reduction in infarct size without histochemical evidence of myocardial neovascularization. The acute hemodynamic study is performed to assess the presence of a vasodilator action of bFGF as described in dogs and other species whereby flow to the infarct zone could possibly be augmented by an increase in the conductance of preexisting collateral channels, independently of neovascularization. In the five dogs studied, coronary blood flow and coronary vascular resistance are unchanged after incremental pharmacological doses of intracoronary bFGF despite pronounced vasodilator responses to 10- and 20-second coronary occlusion and intracoronary NTG. In addition, three of the dogs are monitored for 30 minutes after the final dose of bFGF (100 $\mu$g) to detect the presence of a delayed vasodilator response as reported previously. No significant hemodynamic changes are observed in response to bFGF during the experiment.

Institutional Approval and Sample Size. The protocol is approved by the Cleveland Clinic Foundation Institutional Review Board and Animal Research Committee. Animals are handled in accordance with the National Institutes of Health guidelines for the use of experimental animals. In the occlusion-reperfusion study, 22 dogs are randomized to receive bFGF or vehicle. Five dogs (2 treated with bFGF, 3 with vehicle) die of arrhythmias before completion of the protocol. Three dogs (1 treated with bFGF, 2 with vehicle) are excluded because of persistent occlusion at the site of balloon occlusion. No dogs are excluded from the acute hemodynamic study.

Data Analysis. All data are expressed as mean$\pm$SEM. Differences between groups are evaluated by use of two-tailed, unpaired t tests. The Pearson correlation coefficient is used to assess inter-observer variability for cell counts. Repeated measurements of left ventricular ejection fraction are compared by use of two-way ANOVA. Differences are considered significant at a value of $P<0.05$.

This study demonstrates that bFGF reduces the extent of infarction in the canine occlusion-reperfusion setting. Although there is little doubt that the beneficial effects of bFGF on coronary perfusion in chronic ischemia are mediated principally by its angiogenic actions, we have demonstrated that myocardial salvage occurs independently of neovascularization after administration of bFGF in the setting of acute myocardial infarction. Further evaluation of coronary vasomotor responses to bFGF in ischemic and nonischemic settings and investigation of the potential cytoprotective properties of bFGF in acute ischemia promise to provide fertile and clinically relevant areas for future investigation.

EXAMPLE 7

Intracoronary and Intravenous Administration of FGF-2

This study is designed to investigate the myocardial and tissue deposition and retention of bFGF after IC and i.v. administration in normal and chronically ischemic animals.

Tissue distribution studies are carried out in 24 Yorkshire pigs (12 normal animals and 12 chronically ischemic animals). Yorkshire pigs of either sex weighing 15 to 18 kg are anesthetized with i.m. ketamine (10 mg/kg) and halothane inhalation anesthesia. By sterile technique, a right popliteal cut down is performed and a 4 French arterial catheter is inserted for blood sampling and pressure monitoring. Left thoracotomy is performed through the 4th intercostal space during mechanical ventilation. The pericardium is opened and an ameroid constrictor of 2.5 mm internal diameter (matched to the diameter of the artery) is placed around the proximal left circumflex coronary artery. The pericardium is closed using 6/0 Prolene and the chest is closed. A single dose of i.v. cefazolin (70 mg/kg) is given and i.m. narcotic analgesics are administered as needed. Animals are then allowed to recover for 3 weeks (time sufficient for ameroid closure) before radiolabeled growth factor delivery. The treatment of animals is done according to National Institutes of Health guidelines and the protocol is approved by the Institutional Animal Care and Utilization Committee of the Beth Israel Deaconess Medical Center.

A total of 24 animals are used for the study. Twelve animals undergo ameroid placement on the LCX, and 3 weeks later, after confirming LCX occlusion angiographically, receive $^{125}$I-bFGF. IC $^{125}$I-bFGF is administered to six normal and six ischemic animals, whereas i.v. $^{125}$I-bFGF is given to six normal and six ischemic animals. Tissue deposition is measured at 1 and 24 h in three animals of each group. The use of these two time points is determined by the need to study more sustained myocardial deposition and retention of $^{125}$I-bFGF.

Ischemic animals (three weeks after ameroid placement) and normal noninstrumented animals are anesthetized with i.m. ketamine (10 mg/kg) and halothane inhalation anesthesia. By sterile technique, an i.v. line is inserted into the ear vein and a right femoral cut down is performed to introduce an 8Fr arterial sheath. Coronary angiography is then performed in multiple views using a 7 French JR4 diagnostic catheter (Cordis Laboratories, Inc., Miami, Fla.) to confirm LCX occlusion in ischemic animals and to assess the coronary anatomy. $^{125}$I-Bolton Hunter-labeled bFGF ($^{125}$I-bFGF; 25 $\mu$Ci; New England Nuclear) with a specific activity of 110 $\mu$Ci/$\mu$g (4050 kBq/$\mu$g) is combined with 30 $\mu$g of cold bFGF and 3 mg of heparin (similar to the dose used in animal studies and in the recent phase I IC and i.v. human study) and is used for IC (six normal and six ischemic animals) and i.v. (six normal and six ischemic animals) delivery. For IC delivery, $^{125}$I-bFGF is infused in the left main coronary artery over 10 min. For i.v. delivery, $^{125}$I-bFGF is infused through the ear vein i.v. line over 10 min. Animals are then sacrificed 1 (n=12) and 24 h (n=12) after $^{125}$I-bFGF administration.

Extracardiac Deposition. Biodistribution of the i.v. and IC radiolabeled bFGF is determined at 1 and 24 h after administration and is pooled for ischemic and nonischemic animals. There are no significant differences between ischemic and nonischemic animals at each time point and the data is therefore pooled. At 1 h, the liver accounts for $37.6\pm17.1\%$ of the total administered activity for IC and $42.1\pm17.7\%$ for i.v. delivery (p=0.6), with a reduction to $2.8\pm1.5\%$ for IC and $1.5\pm0.9\%$ for i.v. delivery by 24 h (p=0.09). Total specific activity (1 h) in the kidneys is $2.3\pm1.3\%$ for IC and $2.5\pm1.0\%$ for i.v. delivery (p=0.8). By 24 h, total kidney specific activity decreases to $0.1\pm0.05\%$ for IC and $0.2\pm0.09$ for i.v. delivery (p=0.1). Finally, for IC and i.v. delivery, total lung specific activity is $2.7\pm4.1$ and $3.8\pm2.6\%$ at 1 h (p=0.6) and $0.2\pm0.2$ and $0.4\pm0.08\%$ at 24 h (p=0.05), respectively. Specific activity for urine is $0.01\pm0.01\%$ for IC and $0.005\pm0.01\%$ for i.v. administration at 1 h and increases to 0.02.+−.01% for IC and 0.03.+−.0.05% at 24 h for i.v. delivery, however, that increase is not statistically significant.

Cardiac Deposition. Total specific activity (1 h) was 0.88.+−.0.89% for IC and 0.26.+−.0.08% for i.v. administration (p=0.12) and decreases to 0.05.+−.0.04% (p=0.05, compared with 1 h values) and 0.04.+−.0.01% (p<0.001, compared with 1 h values) at 24 h, respectively. There are no differences between epicardial and endocardial deposition for both IC delivery; the results are pooled for further analysis. For IC delivery, LAD territory activity per gram of tissue (1 h) was 0.01.+−.0.007% and 0.008.+−.0.008% for normal and ischemic animals, and at 24 h drop to 0.0005.+−.0.0009% (20-fold reduction) in nonischemic animals and 0.0008.+−.0.0005% (10-fold reduction) in ischemic animals. For i.v. delivery. 1-h LAD territory activity per gram of tissue is 0.003.+−.0.001% (3-fold reduction, p=0.2, compared with IC) and 0.002.+−.0.0009% (4-fold reduction, p=0.3, compared with IC) for normal and ischemic animals, and at 24 h dropped to 0.0004.+−.0.0001% (7.5-fold reduction) in nonischemic animals and 0.0004.+−.0.0004% (5-fold reduction) in ischemic animals, respectively. For 1-h LCX myocardial deposition, IC and i.v. deliveries result in a specific activity per gram of tissue of 0.008.+−.0.004% and 0.003.+−.0.001% (2.6-fold reduction, p=0.09) in normal animals and 0.01.+−.0.007% and 0.003.+−.0.001% (3.3-fold reduction, p=0.2) in ischemic animals, respectively. At 24 h, LCX deposition for IC and i.v. delivery drop to 0.0006.+−.0.0008% and 0.0005.+−.0.0002% in normal animals and 0.0006.+−.0.0006% and 0.0004.+−.0.0004% in ischemic animals, respectively. For all groups, RCA myocardial distribution is similar to LAD and LCX distribution for i.v. administration. However, for IC delivery, RCA myocardial deposition is significantly lower than LAD or LCX myocardial deposition, because the radiolabel is infused in the left main coronary artery. Finally, for IC delivery, LCX/LAD territory activity is 79% and 154% for nonischemic and isohemic animals at 1 h and 116% and 75% for nonischemic and ischemic animals at 24 h, respectively. Intravenous administration results in an LCX/LAD activity of 97% and 100% for nonisohemic and ischemic animals at 1 h and 123% and 98% for nonischemic and ischemic animals at 24 h. respectively.

Myocardial autoradiography confirms myocardial deposition for both IC and i.v. delivery with three times enhanced deposition for IC delivery compared with i.v. delivery at 1 h with near equalization of tissue deposition at 24 h (measured using densitometric analysis). In addition, IC delivery results in increased deposition in LAD and LCX deposition compared with RCA (noninfused territory) deposition, whereas i.v. delivery results in a more uniform distribution in the three myocardial territories by qualitative analysis. Light level autoradiography after 72-h exposure shows LAD endothelial deposition for IC delivery after 1 h. Evaluation of other arteries for IC delivery at 24 h and for all coronary arteries at all time points fail to show .sup.125 I-bFGF deposition even after 96 h of exposure.

Duplicate plasma, urine (spot samples), and tissue samples from the liver, lung, kidney, and quadriceps muscle are obtained. Tissues are washed three times in saline to avoid contribution of radioactivity in blood. The heart, liver, lungs, and kidneys are weighed to determine total organ weight. Duplicate samples are also obtained from the right ventricle and from the proximal portion of the left anterior descending coronary arteries (LADs) and right coronary arteries (RCAs). A 1-cm mid left ventricular transverse slice is sectioned and cut into eight segments; each segment is divided into epicardial, mid-myocardial, and endocardial portions. .sup.125 I-bFGF activity is determined in a gamma counter (LKB Instruments, Inc., Gaithersburg, Md.). Background is subtracted and the amount of .sup.125 I-bFGF deposited within a specific sample is calculated as a percentage of the total activity administered. Total solid organ deposition is calculated by multiplying the specific activity per gram of tissue by the weight of the organ. Trichloroacetic acid precipitation is performed to determine specific activity, which averaged 86.3.+−.24.4%. A 2-mm transverse left ventricular section is obtained for organ level autoradiography and exposed in a phosphoimager for 24 h. In addition, tissue samples are obtained from the LAD and the subtended myocardium, formalin-fixed, paraffin-embedded, and 10 .mu.m sections are mounted on a slide, coated by a photographic emulsion for 72 h, developed, and examined using light level microscopy.

Data is expressed as mean.+−.S.D. Continuous variables are compared by unpaired Student's t test, whereas categorical variables are compared by .chi.sup.2 analysis. All reported p values are two-tailed; p<0.05 is considered statistically significant.

Both IC and i.v. delivery strategies result in the majority of radiolabel being deposited in the liver. Surprisingly, liver deposition is similar for both techniques, indicating significant recirculation for IC delivery. In addition, these results confirm the previous observation that the liver is the major organ of elimination with circulating bFGF binding to .alpha.-2-macroglobulin, which in turn is internalized by receptors on Kupifer. This result is duplicated for renal and lung deposition. It is important to point out that bFGF is infused in the ear vein (above the diaphragm). However, this simulates i.v. delivery in patients where the port of entry would probably be an upper extremity vein bypassing the liver first pass mechanism. Therefore, IC delivery does not result in less systemic deposition, probably due to high recirculation.

One-hour total and regional myocardial deposition is 3- to 4-fold higher for IC compared with i.v. delivery, and deposition dropped by 5- to 20-fold at 24 h. IC delivery results in higher deposition in ischemic myocardium, possibly related to the increased expression of fibroblast growth factor receptors associated with myocardial ischemia. This is not seen in i.v. delivery, possibly related to the initial concentrations delivered to the ischemic myocardium. Thus IC delivery, by providing higher initial concentrations in the coronary circulation, may result in higher deposition in ischemic areas. These comparisons, although consistent, do not reach statistical significance due to the small number of animals studied.

Of note, IC delivery results in enhanced bFGF deposition compared with i.v. delivery only in myocardial territories subtended by the infused artery. Therefore, for IC delivery to provide an advantage over i.v. delivery, infusion should be carried out in all coronary arteries and bypass grafts if present. Whether infusing a larger dose of bFGF would result in similar myocardial deposition to IC delivery (a more invasive approach) is not investigated. For IC delivery, bFGF is identified on the endothelial cells of the infused arteries, where it might exert its effect. In addition, this study raises an important question of whether more local or sustained delivery is necessary for bFGF effect, particularly with the relatively low cardiac deposition for both delivery modalities.

EXAMPLE 8

Administration of FGF and VEGF to Mobilize Peripheral Blood Stem Cells

A 51 year old male with cardiomiopathy is to receive autologous peripheral blood stem cells to repair his damaged heart. The patient first receives 10 mg VEGF A and 20 mg FGF-1 intravenously daily for five days. Mononuclear cells are collected by apheresis from the patient. The cells are then administered via intracoronary delivery for the treatment of his cardiomyopathy.

As will be readily appreciated from the data given in Example 8, the combined administration of FGF and VEGF produce a substantial increase in the amount of mononuclear cells in the peripheral blood of an individual. It should, in particular, be noticed that the administration of FGF or VEGF alone do not add up to the number of mononuclear cells in the peripheral blood; the combination of FGF and VEGF therefore produces a surprising dose-dependent effect of increasing the number of stem cells, which is not merely the sum of two effects which are independent of each other.

EXAMPLE 9

Administration of AD5FGF-4 to Mobilize Peripheral Blood Stem Cells

A 53 year old white female with cardiomyopathy needs stem cell therapy. Allogenic stem cells are collected from an HLA-matched donor. The donor is a 57 year old white male with chronic calf muscle ischemia. $1 \times 10^{11}$ viral particles of an adenovirus vector AD5FGF-4 are injected into the left calf muscle of the donor. In three weeks the donor stem cells are collected by apheresis. The stem cells are then administered intracoronary for the treatment of the patient's cardiomyopathy.

EXAMPLE 10

Administration of VEGF165 Plasmid DNA to Mobilize Peripheral Blood Stem Cells A 49 year old white female with cardiomyopathy needs stem cell therapy. Allogenic stem cells are collected from an HLA-matched donor. The donor is a 55 year old white male with chronic calf muscle ischemia. 500 µg of VEGF165 plasmid DNA are injected into two different areas of the right calf muscle of the donor (total dose 1000 µg). In three weeks the donor stem cells are collected by apheresis. The stem cells are then administered intracoronary for the treatment of the patient's cardiomyopathy.

Having thus described the invention in rather full detail, it will be understood that such detail need not be strictly adhered to but that various changes and modifications may suggest themselves to one skilled in the art, all falling within the scope of the present invention as defined by the subjoined claims.

What is claimed is:

1. A method for obtaining peripheral blood stem cells (PBSC) comprising the steps of:
    a) administering at least one dose of an effective amount of a therapeutic growth factor protein formulation comprising at least one of the following: FGF1 and FGF2, and also at least one of the following: VEGF, VEGFA and VEGF165, wherein the growth factor formulation is administered by inhalation therapy; and
    b) isolating a population of stem cells from the peripheral blood by apheresis.
2. The method of claim 1 wherein the growth factor formulation is administered in a single dose.
3. The method of claim 1 wherein the growth factor formulation is a dry powder formulation.
4. The method of claim 1 wherein the growth factor formulation is a liquid aerosol formulation.
5. The method of claim 1 wherein the growth factor formulation is administered in repeated doses administered over several days.
6. The method of claim 1 wherein the stem cells are administered to a patient, wherein said patient is the same individual from whom the PBSC were harvested.
7. The method of claim 1 wherein the stem cells are administered to an HLA matched patient.
8. The method of claim 6 which further comprises fractionating the cells prior to implantation.
9. The method of claim 8 wherein the cells are fractionated by fluorescence-activated cell sorting.
10. The method of claim 8 wherein the cells are fractionated by density gradient centrifugation.
11. A method for obtaining peripheral blood stem cells (PBSC), the method comprising the steps of:
    a) administrating at least one dose of an effective amount of a therapeutic growth factor protein formulation comprising at least one of the following: FGF1 and FGF2, and also at least one of the following: VEGF, VEGFA and VEGF165, wherein the growth factor formulation is administered by inhalation therapy; and
    b) isolating a population of stem cells from the peripheral blood by apheresis; and
    c) storing the PBSC for future use.
12. The method of claim 11 wherein the growth factor formulation is administered in a single dose.
13. The method of claim 11 wherein the growth factor formulation is a dry powder formulation.
14. The method of claim 11 wherein the growth factor formulation is a liquid aerosol formulation.
15. The method of claim 11 wherein the growth factor formulation is administered in repeated doses administered over several days.
16. The method of claim 11 wherein the stem cells are administered to a patient, wherein said patient is the same individual from whom the PBSC were harvested.
17. The method of claim 11 wherein the stem cells are administered to an HLA matched patient.
18. A method for obtaining peripheral blood stem cells (PBSC) comprising the steps of:
    a) administering two or more doses of an effective amount of a therapeutic growth factor protein formulation comprising at least one of the following: FGF1 and FGF2, and also at least one of the following: VEGF, VEGFA and VEGF165, wherein the growth factor formulation is first administered by intravenous injection with subsequent administrations by inhalation therapy; and
    b) isolating a population of stem cells from the peripheral blood by apheresis.
19. The method of claim 18 wherein the growth factor formulation is administered in repeated doses administered over several days.
20. The method of claim 18 wherein the stem cells are administered to a patient, wherein said patient is the same individual from whom the PBSC were harvested.
21. The method of claim 18 wherein the stem cells are administered to an HLA matched patient.

22. The method of claim 20 which further comprises fractionating the cells prior to implantation.

23. The method of claim 22 wherein the cells are fractionated by fluorescence-activated cell sorting.

24. The method of claim 22 wherein the cells are fractionated by density gradient centrifugation.

25. A method for obtaining peripheral blood, stem cells (PBSC), the method comprising the steps of:
   a) administrating two or more doses of an effective amount of a therapeutic growth factor protein formulation comprising at least one of the following: FGF1 and FGF2, and also at least one of the following: VEGF, VEGFA and VEGF165, wherein the growth factor formulation is first administered by intravenous injection with subsequent administrations by inhalation therapy; and b) isolating a population of stem cells from the peripheral blood by apheresis; and c) storing the PBSC for future use.

26. The method of claim 25 wherein the growth factor formulation is a dry powder formulation.

27. The method of claim 25 wherein the growth factor formulation is a liquid aerosol formulation.

28. The method of claim 25 wherein the growth factor formulation is administered in repeated doses administered over several days.

29. The method of claim 25 wherein the stem cells are administered to a patient, wherein said patient is the same individual from whom the PBSC were harvested.

30. The method of claim 25 wherein the stem cells are administered to an HLA matched patient.

* * * * *